United States Patent [19]
Finkelstein et al.

[11] Patent Number: 5,312,828
[45] Date of Patent: May 17, 1994

[54] SUBSTITUTED IMIDAZOLES HAVING ANGIOTENSIN II RECEPTOR BLOCKING ACTIVITY

[76] Inventors: Joseph A. Finkelstein; Richard M. Keenan; Joseph Weinstock, all of SmithKline Beecham Corporation, Corporate Patents-U.S. UW2220, P.O. Box 1539, King of Prussia, Pa. 19406-0939

[21] Appl. No.: 746,024

[22] Filed: Aug. 14, 1991

Related U.S. Application Data

[63] Continuation-in-part of Ser. No. 627,177, Dec. 14, 1990, abandoned, which is a continuation-in-part of Ser. No. 505,958, Apr. 6, 1990, abandoned, which is a continuation-in-part of Ser. No. 366,055, Jun. 14, 1989, abandoned.

[51] Int. Cl.$^5$ ............... C07D 233/70; A61K 31/415
[52] U.S. Cl. ................... 514/381; 514/398; 514/399; 514/400; 548/252; 548/253.4; 548/327.1; 548/328.5; 548/329.5; 548/330.1; 548/333.5; 548/334.5; 548/337.1; 548/343.1; 548/343.5; 548/341.1; 548/342.5; 548/338.1
[58] Field of Search ............... 540/251, 252, 253, 336, 540/338, 339, 342, 340; 514/381, 396, 308, 399, 400

[56] References Cited

U.S. PATENT DOCUMENTS

| | | | |
|---|---|---|---|
| 4,340,598 | 7/1982 | Furukawa et al. | 548/342 |
| 4,355,040 | 10/1982 | Furukawa et al. | 548/337 |

FOREIGN PATENT DOCUMENTS

| | | | |
|---|---|---|---|
| 0103647 | 3/1984 | European Pat. Off. | 548/342 |
| 0253310 | 1/1988 | European Pat. Off. | 548/342 |
| 0324377 | 7/1989 | European Pat. Off. | 548/342 |
| WO86/07054 | 12/1986 | PCT Int'l Appl. | 548/342 |

OTHER PUBLICATIONS

Chemical Abstracts vol. 111, No. 19, Abstract 174.092g, p. 724, Nov. 6, 1989.

*Primary Examiner*—C. Warren Ivy
*Assistant Examiner*—Zinna N. Davis
*Attorney, Agent, or Firm*—Mary E. McCarthy; Stephen Venetianer; Edward T. Lentz

[57] ABSTRACT

Angiotensin II receptor antagonists having the formula:

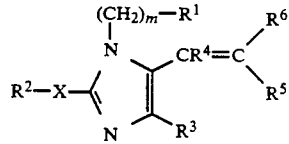

which are useful in regulating hypertension and in the treatment of congestive heart failure, renal failure, and glaucoma, pharmaceutical compositions including these antagonists, and methods of using these compounds to produce angiotensin II receptor antagonism in mammals.

24 Claims, No Drawings

SUBSTITUTED IMIDAZOLES HAVING ANGIOTENSIN II RECEPTOR BLOCKING ACTIVITY

This application is a continuation-in-part of U.S. Ser. No. 07/627,177, filed Dec. 14, 1990 now abandoned, which is a continuation-in-part of U.S. Ser. No. 07/505,958, filed Apr. 6, 1990 now abandoned, which is a continuation-in-part of U.S. Ser. No. 07/366,055, filed Jun. 14, 1989, now abandoned.

The present invention relates to new imidazolyl-alkenoic acids which are angiotensin II receptor antagonists and are useful in regulating hypertension induced or exacerbated by angiotensin II, and in the treatment of congestive heart failure, renal failure, and glaucoma. This invention also relates to pharmaceutical compositions containing imidazolyl-alkenoic acids and methods for using these compounds as antagonists of angiotensin II, as antihypertensive agents and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, exerts stimulation on the release of aldosterone from the adrenal cortex. Therefore, the renin-angiotensin system, by virtue of its participation in the control of renal sodium handling, plays an important role in cardiovascular hemeostasis.

Interruption of the renin-angiotensin system with converting enzyme inhibitors, such as captopril, has proved to be clinically useful in the treatment of hypertension and congestive heart failure (Abrams, W. B., et al., (1984), *Federation Proc.*, 43, 1314). The most direct approach towards inhibition of the reninangiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.*, 6, S176). In addition, recent animal studies suggest that inhibition of the renin-angiotensin system may be beneficial in halting or slowing the progression of chronic renal failure (Anderson, S., et al., (1985), *J. Clin. Invest.*, 76, 612). Also, a recent patent application (South African Patent Application No. 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure and other disorders attributed to the actions of AII. When compounds of this invention are administered to mammals, the elevated blood pressure due to AII is reduced and other manifestations based on AII intercession are minimized and controlled. Compounds of this invention are also expected to exhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

Furukawa et al., U.S. Pat. No. 4,340,598 discloses imidazol-5-ylacetic acids imidazol-5-yl-propanoic acids. Specifically, the disclosure includes 1-benzyl-2-n-butyl-5-chloroimidazole-4-acetic acid and 1-benzyl-2-phenyl-5-chloroimidazole-4-propanoic acid.

Furukawa et al., U.S. Pat. No. 4,355,040 discloses substituted imidazole-5-acetic acid derivatives. A compound specifically disclosed is 1-(2-chlorobenzyl)-2-n-butyl-4-chloroimidazole-5-acetic acid.

Carini et al., in EP 253,310 disclose certain imidazolylpropenoic acids. Two intermediates described in this patent are ethyl 3-[1-(4-nitrobenzyl)-2-butyl-4-chloroimidazol-5-yl]propenoate and ethyl 3-[2-butyl-4-chloro-1-(4-aminobenzyl)imidazol-5-yl]propenoate.

Also, Wareing, in PCT/EP 86/00297, discloses as intermediates certain imidazolylpropenoate compounds. On page 62, Formula (CX) is ethyl 3-[1-(4-fluorophenyl)-4-isopropyl-2-phenyl-1H-imidazol-5-yl]-2-propenoate.

DESCRIPTION OF THE INVENTION

The compounds of the present invention that are blockers of angiotensin II receptors are represented by the following Formula (I):

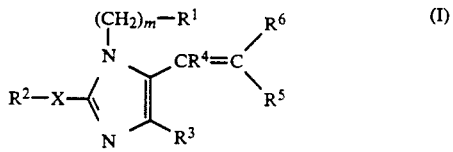

(I)

in which:

R$^1$ is adamantyl, phenyl, biphenyl, or naphthyl, with each aryl group being unsubstituted or substituted by one to three substituents selected from Cl, Br, F, I, $C_1$-$C_6$alkyl, nitro, A-$CO_2R^7$, tetrazol-5-yl, $C_1$-$C_6$alkoxy, hydroxy, $SC_1$-$C_6$alkyl, $SO_2NHR^7$, $NHSO_2R^7$, $SO_3H$, $CONR^7R^7$, CN, $SO_2C_1$-$C_6$alkyl, $NHSO_2R^7$, $PO(OR^7)_2$, $NR^7R^7$, $NR^7COH$, $NR^7COC_1$-$C_6$alkyl, $NR^7CON(R^7)_2$, $NR^7COW$, W, $SO_2W$;

m is 0–4;

R$^2$ is $C_2$-$C_{10}$alkyl, $C_3$-$C_{10}$alkenyl, $C_3$-$C_{10}$alkynyl, $C_3$-$C_6$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R^7$, $CO_2R^7$, CN, $CONR^7R^7$, W, tetrazol-5-yl, $NR^7COC_1$-$C_6$alkyl, $NR^7COW$, $SC_1$-$C_6$alkyl, $SO_2W$, or $SO_2C_1$-$C_6$alkyl;

X is a single bond, S, $NR^7$, or O;

R$^3$ is hydrogen, Cl, Br, F, I, CHO, hydroxymethyl, $COOR^7$, $CONR^7R^7$, $NO_2$, W, CN, $NR^7R^7$, or phenyl;

R$^4$ and R$^5$ are independently hydrogen, $C_1$-$C_6$alkyl, phenyl-Y-, naphthyl-Y-, or biphenyl-Y-, wherein the aryl groups are unsubstituted or substituted by one to three substituents selected from Cl, Br, F, I, $C_1$-$C_6$alkoxy, hydroxy, $CO_2R^7$, CN, $NO_2$, tetrazol- 5-yl, $SO_3H$, $CF_3$, $CONR^7R^7$, $SO_2NHR^7$, $C_1$-$C_6$alkyl, or $NR^7R^7$, or by methylenedioxy, phenoxy or phenyl, except that $R^4$ and $R^5$ are not both selected from hydrogen;

Y is a single bond, O, S, or $C_1$-$C_6$alkyl which is straight or branched or optionally substituted by phenyl or benzyl, wherein each of the aryl groups is unsubstituted or substituted by halo, $NO_2$, $CF_3$, $C_1$-$C_4$alkyl, $C_1$-$C_4$alkoxy, CN, or $CO_2R^7$;

$R^6$ is —Z—$COOR^8$ or —Z—$CONR^7R^7$;

Z is a single bond, vinyl, —$CH_2$—O—$CH_2$—, methylene optionally substituted by $C_1$-$C_4$alkyl, one or two benzyl groups, thienylmethyl, or furylmethyl, or —C(O)NHCHR$^9$—, wherein $R^9$ is H, $C_1$-$C_4$alkyl, phenyl, benzyl, thienyl-methyl, or furylmethyl;

each $R^7$ independently is hydrogen, $C_1$-$C_4$alkyl, or $(CH_2)_m$phenyl, wherein m is 0–4; and $R^8$ is hydrogen, $C_1$-$C_6$alkyl, or 2-di($C_1$-$C_4$alkyl)amino-2-oxoethyl; or $R^5$ and $R^6$ are both hydrogen, $R^4$ is —Z—$COOR^8$ and Z is other than a single bond; or a pharmaceutically acceptable salt thereof.

Preferably, one of $R^4$ and $R^5$ is hydrogen or $C_1$-$C_6$-alkyl.

Preferred compounds of this invention are represented by Formula (I) when:

$R^1$ is phenyl unsubstituted or substituted by one to three substituents selected from chloro, fluoro, trifluoromethyl, nitro, methyl, methoxy, hydroxy, sulfamyl, carboxy, carbo$C_1$-$C_4$alkoxy, carbamoyl, cyano, or tetrazol-5-yl;

m is 0-b 2;

X is a single bond or S;

$R^2$ is $C_2$-$C_8$alkyl;

$R^3$ is hydrogen, chloro, fluoro, or trifluoro-methyl;

$R^4$ is hydrogen or $C_1$-$C_4$alkyl;

$R^5$ is $C_3$-$C_5$alkyl or benzyl unsubstituted or substituted by one to three substituents selected from Cl, Br, F, $NO_2$, $OCH_3$, OH, $CF_3$, $NR^7R^7$, $CH_3$, or $CO_2R^7$, or methylenedioxy;

$R^6$ is COOH;

each $R^7$ independently is H or $CH_3$;

or a pharmaceutically acceptable salt thereof.

The E isomers (trans stereochemistry of the carboxy and imidazole groups) are generally more active and thus, are preferred over the Z isomers (cis).

As used herein, the terms alkyl, alkenyl, alkoxy, and alkynyl mean carbon chains which are branched or unbranched with the length of the chain determined by the descriptor preceding the term.

Particular compounds of the invention include, but are not limited to, the following:

(E)-3-[2-n-butyl-1-{(2-chlorophenyl)methyl}-1H-imidazol-5-yl]-2-benzyl-2-propenoic acid, (E)-3-[2-n-butyl-1-{(2-chloro-6-fluorophenyl)methyl}-1H-imidazol-5-yl]-2-benzyl-2-propenoic acid, (E)-3-[2-n-butyl-1-{(2-chlorophenyl)methyl}-1H-imidazol-5-yl]-2-(3,4-dimethoxyphenyl)methyl-2-propenoic acid, (E)-3-[2-n-butyl-1-{(2-chlorophenyl)methyl}-1H-imidazol-5-yl]-2-(3,4-methylenedioxyphenyl)methyl-2-propenoic acid, (E)-3-[2-n-butyl-1-{(2-chlorophenyl)methyl}-1H-imidazol-5-yl]-2-(4-methoxyphenyl)methyl-2-propenoic acid, (E)-3-[2-n-butyl-1-{(2-chlorophenyl)methyl}-4-chloro-1H-imidazol-5-yl]-2-benzyl-2-propenoic acid, (E)-3-[2-n-butyl-1-{(2-chlorophenyl)methyl}-1H-imidazol-5-yl]-2-(3,4-dihydroxyphenyl)methyl-2-propenoic acid, (E)-3-[2-n-butyl-1-{(2-chlorophenyl)methyl}-1H-imidazol-5-yl]-2-(2-nitrophenyl)methyl-2-propenoic acid, (E)-3-[2-n-butyl-1-{(2-chlorophenyl)methyl}-1H-imidazol-5-yl]-2-(4-N,N-dimethylaminophenyl)methyl-2-propenoic acid, (E)-3-[2-n-butyl-1-{(4-carboxyphenyl)methyl}-1H-imidazol-5-yl]-2-n-butyl-2-propenoic acid, (E)-3-[2-n-butyl-1-{(4-carboxyphenyl)methyl}-1H-imidazol-5-yl]-2-benzyl-2-propenoic acid, and (E)-3-[2-n-butyl-1-{(2-chlorophenyl)methyl}-1H-imidazol-5-yl]-2-(4-aminophenyl)methyl-2-propenoic acid; or a pharmaceutically acceptable salt thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of producing antihypertensive activity and methods of treating congestive heart failure, glaucoma, and renal failure by administering these compounds are also included in this invention.

The compounds of this invention and of the pharmaceutical compositions and methods of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule The starting materials, 2-$R^2$X-imidazole, are known to the art (J. Org. Chem. 45:4038, 1980) or are synthesized by known procedures. For example, imidazole is converted to 2-n-butylimidazole by reacting imidazole with triethylorthoformate and p-toluenesulfonic acid to give 1-diethoxyorthoamide imidazole and then treating with n-butyl lithium to give the 2-lithium derivative of the orthoamide and alkylating with n-butyl iodide in a suitable solvent, such as tetrahydrofuran (THF).

The following procedure is useful for the preparation of compounds of Formula (I) particularly where $R^1$ is 2-chlorophenyl or 4-carboxyphenyl, $R^2$ is n-butyl or n-propyl, X is a single bond or S, $R^3$ is hydrogen, chloro, or $CF_3$, $R^4$ is hydrogen, $R^5$ is as described in Formula (I), $R^6$ is $COOR^8$ and $R^8$ is hydrogen, methyl, or ethyl.

The 1-$R^1$($CH_2$)$_m$-group is incorporated onto the 2-$R^2$X-imidazole by known procedures, for example, by reaction with an $R^1$—($CH_2$)$_m$-halide, mesylate or acetate, such as 2-chlorobenzylbromide, in a suitable solvent, such as dimethylformamide (DMF), in the presence of a suitable acid acceptor, such as sodium alkylate, potassium or sodium carbonate, or a metal hydride, preferably sodium hydride at a reaction temperature of about 25° C. to about 100° C., preferably at about 50° C. The resulting 1-$R^1$($CH_2$)$_m$-2-$R^2$X-imidazole is hydroxymethylated in the 5-position, for example, by reacting with formaldehyde in the presence of sodium acetate in acetic acid to provide the 1-$R^1$($CH_2$)$_m$-2-$R^2$X-5-hydroxymethyl-imidazole intermediates.

Alternatively, the 1-$R^1$($CH_2$)$_m$-2-$R^2$-5-hydroxymethylimidazole intermediates are prepared by reacting an imido ether, $R^2$—C(=NH)—O-alkyl, such as valeramidine methyl ether, with dihydroxyacetone in liquid ammonia under pressure to give 2-$R^2$-5-hydroxymethyl-imidazole. This intermediate is reacted with acetic anhydride to give 1-acetyl-5-acetoxymethyl-2-$R^2$-imidazole. The diacetate intermediate is N-alkylated, for example, using 2-chlorobenzyl triflate and the resulting 1-$R^1$($CH_2$)$_m$-2-$R^2$-5-acetoxymethylimidazole is treated with aqueous base, such as 10% sodium hydroxide solution to give the 1-$R^1$($CH_2$)$_m$-2-$R^2$-5-hydroxymethyl-imidazole intermediate.

Alternatively, the 2-$R^1$S-imidazole compounds are prepared by the following procedure. Benzylamines, substituted by one to three substituents selected from halo, $C_{1-6}$alkyl, $C_{1-6}$alkoxy, CN, $NO_2$, $CF_3$, $CO_2C_{1-6}$alkyl, $SC_{1-6}$alkyl, or $SO_2C_{1-6}$alkyl, are alkylated with a $C_{1-6}$alkyl chloroacetate, for example methyl chloroacetate, in the presence of a base, such as triethylamine, in a suitable solvent, such as dimethylformamide. The resulting alkylaminoalkyl ester compounds are N-formulated with formic acid in the presence of a suitable solvent, such as xylenes, followed by C-formulation of the carbon alpha to both the amino and the ester groups. Reaction of this intermediate with acidic thiocyanate, preferably potassium thiocyante, in an inert organic solvent, such as a $C_{1-4}$alkyl alcohol, produces 1-$RCH_2$-2-mercapto-5-alkanoate ester imidazole compounds. The free thio group of the ester imidazole is reacted with a halo-$R^{10}$ compound, wherein $R^{10}$ is $C_{2-10}$alkyl, $C_{3-10}$alkenyl, $C_{3-10}$alkynyl, $C_3$-$C_6$cycloalkyl or an optionally substituted ($CH_2$)$_{0-8}$phenyl, preferably propyl bromide, in the presence of a suitable base, such as sodium carbonate, in an appropriate solvent, such as ethyl acetate. The ester is reduced to the hydroxymethylimidazole intermediate by reduction with a suitable reagent, preferably diisobutyl aluminum hydride, in an appropriate solvent, such as tetrahydrofuran, at a temperature of about −78° C. to about 25° C., preferably at less than −10° C.

The hydroxymethyl group of the hereinbefore prepared intermediate is oxidized to an aldehyde by treatment with a suitable reagent, such as anhydrous chromic acid-silica gel in tetrahydrofuran or, preferably, with activated manganese dioxide, in a suitable solvent such as benzene, or toluene, or preferably methylene chloride, at a temperature of about 25° C. to about 140° C., preferably at about 25° C. The 1-$R^1$($CH_2$)$_m$-2-$R^2$X-imidazol-5-carboxaldehydes are reacted with an appropriate phosphonate, such as those listed in Table I. The phosphonates are prepared, for example, from trialkyl phosphonoacetates by alkylation with an appropriate halide, mesylate or acetate in the presence of a suitable base, such as sodium hydride, in a suitable solvent, preferably glyme at a reaction temperature of about 25° C. to about 110° C., preferably at about 55° C., to provide, for example, the phosphonates listed in Table I. The reaction of the imidazol-5-carboxaldehydes with the phosphonates is performed in the presence of a suitable base, such as a metal alkoxide, lithium hydride or, preferably, sodium hydride, in a suitable solvent, such as ethanol, methanol, ether, dioxane, tetrahydrofuran or, preferably glyme, at a reaction temperature of about 10° C. to about 50° C., preferably, at about 25° C., to provide a variable mixture of tarns and cis, e.g., (E) and (Z), 1-$R^1$($CH_2$)$_m$-2-$R^2$X-5-CH=C($R^5$)(COOalkyl)-imidazoles. These isomers are readily separated by chromatography over silica gel in suitable solvent systems, preferably hexane in ethyl acetate mixtures. The esters are hydrolyzed to the acids, 1-$R^1$—($CH_2$)$_m$2-$R^2$X-5-CH=C($R^5$)COOH-imidazoles, using a base, such as potassium hydroxide, lithium hydroxide or sodium hydroxide, in a suitable solvent system, such as, for example, aqueous alcohols or diglyme. The trans and cis structures of the acids are readily determined by NMR by the NOE protocol, as well as by the biological activities since, generally, the trans (E) isomeric acids are the more potent isomers.

Alternatively, the 1-$R^1$($CH_2$)$_m$-2-$R^2$X-imidazol-5-carboxaldehydes are prepared by the following procedure. Starting 2-$R^2$X-imidazol-5-carboxaldehydes are reacted with an N-alkylating protecting reagent, such as chloromethyl pivalate (POM-Cl), in the presence of a base, such as potassium carbonate, in a suitable solvent, such as dimethylformamide, at a temperature of about 20° C. to about 50° C., preferably at about 25° C., to give N-alkylation (e.g., POM-derivation) on the least hindered nitrogen atom of the imidazole nucleus. The 1-$R^1$($CH_2$)$_m$-group is incorporated onto the imidazole by N-alkylation of the above prepared aldehyde with a halomethylbenzene compounds, such as methyl 4-bromomethyl-3-chlorobenzoate, at a temperature of about 80° C. to about 125° C., preferably at about 100° C. The protecting group on the 3-nitrogen of the imidazole ring is removed by base hydrolysis, for example using a biphasic mixture of ethyl acetate and aqueous sodium carbonate, to give 1-$R^1$($CH_2$)$_m$-2-$R^2$X-imidazole-5-carboxaldehyde compounds. The Formula (I) compounds can be prepared from these 5-carboxaldehyde compounds by the methods described above.

Compounds of Formula (I) wherein $R^6$ is $COOR^8$, $R^1$, $R^2$, $R^3$, $R^4$ and $R^5$ are as described in Formula (I), and $R^8$ is H, methyl or ethyl, are also prepared by the following procedure.

The 2-$R^2$X-imidazole starting materials are reacted with trimethylsilylethoxymethyl (SEM) chloride to give 1-(trimethylsilyl)ethoxymethyl- 2-$R^2$X-imidazole. The reaction is carried out, for example, in the presence of sodium hydride in a solvent such as dimethylformamide. The 5-tributyltin derivatives are prepared by lithiation with, for example, butyllithium in a suitable solvent, preferably diethyl ether, followed by treatment of the lithio imidazole derivative with a tributyltin halide, preferably tri-n-butyltin chloride, at about −10° C. to about 35° C., preferably at about 25° C. The 1-SEM-2-$R^2$X-5-tributyltin-imidazole is coupled with an α,β-unsaturated acid ester having a leaving group on the β-position, such as a halide or trifluoromethanesulfonyloxy group, for example, $BrCR^4$=C($R^5$)(COOalkyl), in the presence of a phosphine ligand, such as bis(diphenylphosphino)propane, or triphenylphosphine and a palladium (II) compound, or preferably tetrakis(triphenylphosphine)palladium(0), and with or without a base, such as tributylamine, at a temperature of about 50° C. to about 150° C., preferably at about 120° C. Both the (E) and (Z) olefinic isomers are prepared by this procedure, and the isomeric esters are readily separated by chromatography over silica gel. The 1-SEM group from the (E) and (Z) isomers is hydrolyzed with acid, for example, aqueous hydrochloric, in a suitable alcoholic solvent, such as methanol or ethanol, and the 1-unsubstituted imidazole derivatives are converted to the 1-t-butoxycarbonyl (t-BOC) imidazoles with di-t- butyl dicarbonate (Hoppe-Seyler's Z. *Physiol. Chem.*, (1976), 357, 1651). The t-BOC esters are alkylated and hydrolyzed with, for example, 2-chlorobenzyl-O-triflate in the presence of a suitable base, preferably diisopropylethyl-amine, in a suitable solvent, preferably methylene chloride, to afford the 1-[(2-chlorophenyl)-methyl]-imidazole derivatives (esters). The (E) and (Z) isomers of the esters are hydrolyzed to the (E) and (Z) acids by the method described above.

Compounds of Formula (I) are also prepared by the following procedure. The 1-$R^1(CH_2)_m$-2-$R^2X$-imidazol-5-carboxaldehydes, prepared as described above, are reacted with a substituted half-ester, half-acid derivative of a malonate, such as ethyl 2-carboxy-3-phenylpropionate, in the presence of a base, such as piperidine, in a suitable solvent, such as toluene, at a temperature of about 80° C. to about 110° C., preferably at about 110° C. The resulting 1-$R^1(CH_2)_m$-2-$R^2X$-5-CH=C($R^5$)COOalkyl)imidazoles are hydrolyzed to the corresponding Formula (I) acid compounds by alkaline hydrolysis as described above.

Compounds of Formula (I) in which $R^1$ is 2-chlorophenyl or 4-carboxyphenyl, $R^2$ is n-butyl or n-propyl, X is a single bond or S, $R^3$ is H, Cl, or $CF_3$, $R^4$ is methyl, $R^5$ is as described in Formula (I), $R^6$ is $COOR^8$ and other parameters are as described above are prepared as follows. The 1-$R^1(CH_2)_m$-2-$R^2X$-imidazol-5-carboxaldehydes, prepared as described above, are converted to the corresponding alcohols with an organometallic derivative or Grignard reagent, preferably methyl lithium, in a suitable solvent, such as tetrahydrofuran. The alcohol is oxidized, for example, using manganese dioxide to give the ketone. The olefinic esters are prepared from the ketone by reaction with appropriate phosphonates to give the (E) and/or (Z) isomers which are readily separated. The acids are prepared from the esters by alkaline hydrolysis as described above.

Compounds of Formula (I) are also prepared as follows. The 1-$R^1(CH_2)_m$-2-$R^2X$-imidazol-5-carboxaldehydes are treated with the lithium derivative of a substituted ethyl or methyl ester. These lithio derivatives are prepared from the reaction of lithium diisopropylamide in a suitable solvent, preferably tetrahydrofuran, with an acid ester, such as ROOC—$CH_2$—Y-phenyl, to generate the a-lithio derivatives at about $-78°$ C. to about $-10°$ C., preferably at about $-78°$ C., which are then treated with the imidazol-carboxaldehyde. The intermediate β-hydroxy group of the imidazole ester is converted to a mesylate or an acetate and the mesylate, or preferably the acetate, is heated in a suitable solvent, such as toluene, with one to two equivalents of 1,8-diazobicyclo[5.4.0]undec-7-ene, at about 50° C. to about 110° C., preferably at about 80° C., to afford ester compounds of Formula (I) such as 3-(imidazol-5-yl)-2-benzyl-2-propenoic acid esters. The (E) isomer is the predominate olefinic isomer The acids are prepared from the esters by the method described above.

Compounds of Formula (I) wherein $R^1$ is 2-chlorophenyl or 4-carboxyphenyl, $R^2$ is n-butyl or n-propyl, X is a single bond or S, $R^3$ is H, Cl, $CF_3$, or $CH_2OH$, $R^4$ is H, $R^5$ is an aryl or a substituted aryl group as described in Formula (I) and $R^6$ is COOH, may be prepared by heating 1-$R^1(CH_2)_m$-2-$R^2X$-imidazol-5-carboxaldehydes at about 50° C. to about 180° C., preferably at about 140° C., with an appropriate substituted aryl acetic acid an.d with acetic anhydride and potassium carbonate to provide unsaturated acids of Formula (I), such as 3-[2-n-butyl-1-(2-chlorophenyl)methyl-1H-imidazol-5-yl]-2-$R^5$-2-propenoic acid. The trans olefinic acid is the principal product.

Compounds of Formula (I) in which $R^6$ is Z—$COOR^8$ where Z is an optionally substituted methylene group are prepared by reducing the trans or (E) isomers of 3-(imidazol-5-yl)-2-propenoic acid esters (prepared as described above) with an appropriate hydride reagent, preferably diisobutylaluminum hydride, in a suitable solvent, such as tetrahydrofuran, to provide the unsaturated alcohol compounds (5-HOCH$_2$CH=CH-imidazoles). These compounds are reacted with ethyl chloroformate, for example, with a base, preferably triethylamine, in a suitable solvent, such as tetrahydrofuran, to give 5-EtOOCOCH$_2$CH=CH-imidazoles which are reacted with carbon monoxide in the presence of a phosphine ligand, preferably triphenylphosphine with palladium (II) acetate, in a suitable solvent, preferably tetrahydrofuran, at a temperature of about 25° C. to about 100° C., preferably at about 40° C., to give the 5-EtOOCCH$_2$CH=CH-imidazoles. The corresponding acids are prepared from these ethyl esters by base hydrolysis as described above.

Compounds of Formula (I) in which Z is —CH$_2$COOR$^8$ having additional substitution on the carbon a to the carboxylate group are prepared by converting 5-EtOOCH$_2$CH=CH-imidazoles to the lithium derivative of the ester with a lithium dialkylamide, preferably lithium diisopropylamide, and then treating with an alkylating agent, such as methyl halide, benzyl bromide, or heterocyclic methyl halide, to provide the monoalkylated product compounds or the dialkylated product compounds. The acid compounds are prepared from the esters by base hydrolysis.

Compounds of Formula (I) in which $R^6$ is Z—$COOR^8$ where Z is —CH$_2$—O—CH$_2$— are prepared from the above-prepared unsaturated alcohol compounds which had been obtained by the reduction of the Formula (I) propenoic acid esters. The alcohol is reacted with an appropriate hydride reagent, such as sodium hydride, in a suitable solvent, such as glyme, followed by reaction with an alkylating reagent, such as methyl bromoacetate to give the 5-MeOOCCH$_2$—O—CH$_2$CR$^5$=CR$^4$-imidazoles. The corresponding acids are prepared from these esters by base hydrolysis as described above.

Compounds of Formula (I) in which $R^6$ is Z—$COOR^8$ where Z is —C(0)NHCHR$^9$— are prepared from the Formula (I) propenoic acid compounds. These acids are reacted with an appropriately substituted amino acid, such as glycine methyl ester hydrochloride or phenylalanine methyl ester hydrochloride, in the presence of an amide-forming reagent, such as N-hydroxysuccinimide and dicyclohexylcarbodiimide in the presence of a base, for example triethylamine, in a suitable solvent, such as tetrahydrofuran, at a temperature of about 20° C. to about 50° C., preferably at about 35° C. The 5-$C_{1-4}$ alkylOOCCHR$^9$NH-C(O)—CH$_2$CR$^5$=CR$^4$-imidazoles are converted to their corresponding acids by base hydrolysis as described above.

Compounds of Formula (I) in which the $R^1$ substituent is substituted by hydroxy are formed from Formula (I) compounds in which the $R^1$ group is substituted by $C_1$-$C_4$alkoxy using an ether-cleaving reagent, such as boron tribromide or hydrobromic acid.

Compounds of Formula (I) in which the $R^1$ substituent is substituted by carboxy are formed from Formula (I) compounds in which the $R^1$ grou is substituted by $CO_2C_1$–$C_4$alkyl using basic hydrolysis, such as aqueous sodium or potassium hydroxide in methanol or ethanol, or using acidic hydrolysis, such as aqueous hydrochloric acid.

Compounds of Formula (I) in which the $R^1$ substituent is substituted by a tetrazol-5-yl group are prepared from the corresponding carboxy compounds. For example, the Formula (I) acid compounds are reacted with a halogenating agent, such as thionyl chloride in a suitable solvent, for example benzene, to give the corresponding acid halide compounds. The acid halides are then converted to primary amide compounds in a reaction with concentrated ammonia. Subsequent dehydration of the amides with oxalyl chloride/dimethylformamide in acetonitrile/dimethylformamide yields the nitrile compounds, which are the immediate precursors to the Formula (I) tetrazole compounds. Tetrazole formation is accomplished by reacting the nitriles with azide, preferably aluminum azide prepared in situ by the reaction of sodium azide with aluminum chloride, in a suitable solvent, for example tetrahydrofuran. The Formula (I) compounds in which $R^6$ is —Z—$CO_2H$ are prepared from these Formula (I) tetrazole ester compounds by base hydrolysis as described above.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids Pharmaceutically acceptable base addition salts of compounds of Formula (I) in which $R^8$ is H are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperzine, meglumine, choline, diethanolamine, and tromethamine.

Angiotensin II antagonist activity of the compounds of Formula (I) is assessed by in vitro and in vivo methods. In vitro antagonist activity is determined by the ability of the compounds to compete with $^{125}I$-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

Binding

The radioligand binding assay is a modification of a method previously described in detail (Gunther et al., Circ. Res. 47:278, 1980). A particular fraction from rat mesenteric arteries is incubated in Tris buffer with 80 pM of $^{125}I$-angiotensin II with or without angiotensin II antagonists for 1 hour at 25° C. The incubation is terminated by rapid filtration and receptor bound $^{125}I$-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. Exemplary of the $IC_{50}$ of compounds of the invention (E isomers) is about 4 nM to about 100 μM.

Aorta

The ability of the compounds to antagonize angiotensin II induced vasoconstriction is examined in the rabbit aorta. Ring segments are gut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants ($K_B$) are calculated by the dose ratio method using the mean effective concentrations. Exemplary of the $K_B$ of compounds of the invention (E isomers) is about 0.4 nM to about 25 μM.

Inhibition of Pressor Response to Angiotensin II in Conscious Rats

Rats are prepared with indwelling femoral arterial and venous catheters and a stomach tube (Gellai et al., Kidney Int. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 3 to 300 mg/kg. The dose of compound needed to produce 50% inhibition of the control response to angiotensin II ($IC_{50}$) is used to estimate the potency of the compounds. The $IC_{50}$ of (E)-2-n-butyl-1-{(2-chlorophenyl)methyl}-1H-imidazol-5-yl]-2-benzyl-2-propenoic acid is 14 mg/kg i.v.

Antihypertensive Activity

The antihypertensive activity of the compounds is measured by their ability to reduce mean arterial pressure in conscious rats made renin-dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intra-venously or orally. The dose of compound needed to reduce mean arterial pressure by 30 mm Hg ($IC_{30}$) is used as an estimate of potency. The $IC_{30}$ of (E)-3-[2-n-butyl-1-{(2-chlorophenyl)methyl}-1H-imidazol-5-yl]-2-benzyl-2-propenoic acid is 10 mg/kg i.v.

The intraocular pressure lowering effects employed in this invention may be measured by the procedure described by Watkins, et al., J. Ocular Pharmacol., 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmolgic administration, the pharmaceutical compositions adapted include solutions, suspensions, ointments, and solid inserts Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components such as quarternary ammonium compounds; buffering ingredients such as alkali metal chloride; antioxidants such as sodium metabisulfite; and other conventional ingredients such as sorbitan monolaurate.

Additionally, suitable ophthalmic vehicles can be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, nontoxic quantity selected from the range of 0.01-200 mg/kg of active compound, preferably 1-100 mg/kg. The selected dose is administered to a human patient in need of angiotensin II receptor antagonism from 1-6 times daily, orally, rectally, topically, by injection, or continuously by infusion. Oral dosage units for human administration preferably contain from 10 to 500 mg of active compound. Preferably, lower dosages are used for parenteral administration. Oral administration, at higher dosages, however, also can be used when safe and convenient for the patient. Topical formulations contain the active compound in an amount selected from 0.0001 to 0.1 (w/v%), preferably from 0.0001 to 0.01. As a topical dosage unit form, an amount of active compound from between 50 ng to 0.05 mg, preferably 50 ng to 5 mg, is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the methods of treating congestive heart failure, glaucoma, and renal failure comprise administering a compound of Formula (I) to a subject in need of the indicated activity in an effective amount to produce said activity.

Contemplated equivalents of Formula (I) compounds are compounds otherwise corresponding thereto wherein substituents have been added to any of the unsubstituted positions of the Formula (I) compounds provided such compounds have the pharmaceutical utility of Formula (I) compounds.

The following examples illustrate preparation of compounds and pharmaceutical compositions of this invention. The examples are not intended to limit the scope of this invention as defined hereinabove and as claimed below.

EXAMPLE 1

(E)-3-2-n-Butyl-1-}(2-chlorophenyl)methyl}-1H-imidazol-5-yl]-2-methyl-2-propenoic Acid (i) 2-n-butyl-1-(2-chlorophenyl)methyl-1H-imidazole Imidazole was converted to the 1-diethoxyorthoamide derivative by the method of Curtis and Brown, *J. Org. Chem.*, (1980), 45, 20. Imidazole (12.8 g, 0.19 mol) and 118.4 g (0.8 mol) of triethylorthoformate were reacted in the presence of 1 g of p-toluenesulfonic acid to give 20.6 (61%), bp 65°-70° C. (0.1 mm) of 1-diethoxyorthoamide imidazole. This product (24.0 g, 0.14 mol) was dissolved in dry tetrahydrofuran (250 mL), cooled to −40° C. and n-butyl lithium (0.14 mol, 56.4 mL of 2.5 M in hexane) was added at −40° C. to −35° C. After 15 minutes n-butyl iodide (31.1 g, 0.169 mol) was added at −40° C., and the reaction was stirred overnight at ambient temperature. The reaction was partitioned between ether and 0.3 N hydrochloric acid, and the organic layer was repeatedly extracted with dilute hydrochloric acid. The combined aqueous extracts were neutralized with sodium bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 mL) and added dropwise to a solution of sodium methoxide (from sodium hydride (2.31 g, 0.0934 mol) in methanol (250 mL)). After one hour the solution was evaporated to dryness, and the sodium salt was taken up in dry dimethylformamide (150 mL) and 2-chlorobenzyl bromide (16.3 g, 0.079 mol) was added. The mixture was heated at 50° C. for 17 hours under argon, poured onto ice water and the product was extracted into ethyl acetate. The extract was washed, dried, and concentrated to give 18.5 g of crude product which was chromatographed over silica gel with 2:1 ethyl acetate/hexane to provide 11.9 g (61%) of 2-n-butyl-1-(2-chlorophenyl)methyl-1H-imidazole as an oil. Thin layer chromatography on silica gel with 4:1 ethyl acetate/hexane gave an $R_f$ value of 0.59.

(ii)
2-n-butyl-1-(2-chlorophenyl)methyl-5-hydroxymethyl-1H-imidazole

Method A

A mixture of 2-n-butyl-1-(2-chlorophenyl)methyl-1H-imidazole (95.5 g, 0.384 mol), 37% formaldehyde (500 mL), sodium acetate (80 g) and acetic acid (60 mL) was heated to reflux for 40 hours under argon The reaction was concentrated in vacuo, and the residue was stirred with 500 mL of 20% sodium hydroxide solution for 4 hours, diluted with water and extracted with methylene chloride The extract was washed, dried, and concentrated. The crude product (117 g) was flash chromatographed over 600 g of silica gel with a gradient of ethyl acetate to 10% of methanol in ethyl acetate to give 8.3 g of starting material, 24.5 g of a mixture of starting material and product, and 44 g (41%) of 2-n-butyl-1-(2-chlorophenyl)methyl-5-hydroxymethyl-1H-imidazole; mp 86°–88° C. (from ethyl acetate) Further elution provided the bis (4,5-hydroxymethyl) derivative; mp 138°–140° C. (from ethyl acetate).

Method B

A mixture of valeramidine methyl ether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3 L). The resulting slurry was refluxed with added acetonitrile (1 L). The solution was decanted from the solid ammonium chloride while hot. This procedure was repeated, and the combined acetonitrile extracts were treated with charcoal, filtered hot and the filtrate was concentrated in vacuum to give the dark oil, 2-n-butyl-5-hydroxymethylimidazole (253 g, 1.63 mol, 98%).

This crude alcohol (253 g) was treated with acetic anhydride (400 mL) at −15° C. and then was allowed to warm to ambient temperature with stirring, and then stirred an additional 19 hours. The acetic anhydride was evaporated at reduced pressure, the residue taken up in methylene chloride, and the organic phase was washed with 5% sodium bicarbonate solution and water. The extract was dried over sodium sulfate and concentrated to give 323 g (83%) of 1-acetyl-4-acetoxymethyl-2-n-butylimidazole.

This diacetate was N-alkylated by the following procedure. To a solution of triflic anhydride (120 mL, 0.71 mol) in methylene chloride (200 mL) at −78° C. under argon was added a solution of diisopropyl ethylamine (128 mL, 0.73 mol) and 2-chlorobenzyl alcohol (104 g, 0.72 mol) in methylene chloride (350 mL) over a period of 20

After being stirred an additional 20 minutes at −78° C., this solution was then treated with 1-acetyl-4-acetoxymethyl-2-n-butylimidazole (146 g, 0.61 mol) dissolved in methylene chloride (300 mL) over a 20-minute interval. The mixture was then stirred at ambient temperature for 18 hours and the solvents were evaporated.

The residual 2-n-butyl-5-acetoxymethyl-1-(2-chlorophenyl)methyl-1H-imidazole was used without purification for the hydrolysis of the acetate group.

A solution of crude 2-n-butyl-5-acetoxymethyl-1-(2-chlorophenyl)methyl-1H-imidazole (250 g) in methanol (200 mL) was treated with 10% sodium hydroxide solution (700 mL) and the mixture was heated on a steam bath for 4 hours. After cooling, methylene chloride was added, the organic phase was separated, washed with water, dried and concentrated. The residue was dissolved in ether, cooled, and seeded to give the crude product. Recrystallization from ethyl acetate gave 176 g of 2-n-butyl-1-(2-chlorophenyl)methyl-5-hydroxymethyl-1H-imidazole; mp 138°–140° C. This material was identical in all respects to the product prepared by Method A.

(iii)
2-n-butyl-1-(2-chlorophenyl)methyl-1H-imidazol-5-carboxaldehyde

A solution of 2-n-butyl-1-(2-chlorophenyl)methyl-5-hydroxymethyl-1H-imidazole (5.4 g, 0.0194 mol) in methylene chloride (25 mL) was added to a suspension of activated manganese dioxide (27 g) in methylene chloride (325 mL). The suspension was stirred at room temperature for 17 hours. The solids were filtered and the filtrate concentrated and flash chromatographed over silica gel with 6:4 hexane/ethyl acetate to afford 4.16 g (78%) of 2-n-butyl-1-(2-chlorophenyl)methyl-1H-imidazol-5-carboxaldehyde, as an oil. NMR and IR were consistent with the structure.

(iv) ethyl
(E)-3-[2-n-butyl-1-{(2-chlorophenyl)methyl}1H-imidazol-5-yl]-2-methyl-2-propenoate Ethanol (5 mL) was treated with sodium metal (0.101 g, 0.0044 g-atom), then triethyl 2-phosphonopropionate (0.953 g, 0.004 mol) in ethanol (2 mL) was added. After 5 minutes a solution of 2-n-butyl-1-(2-chlorophenyl)-methyl-1H-imidazol-5-carboxaldehyde (1.1 g, 0.004 mol) in ethanol (2 mL) was added to give an initial exotherm The reaction mixture was stirred at ambient temperature under argon for 2 hours, concentrated in vacuo and the residue partitioned between water and ethyl acetate. The extract was washed, dried, and concentrated. The crude product was flash chromatographed over silica gel with an ethyl acetate/hexane gradient to provide ethyl (E)-3-[2-n-butyl-1-{(2-chlorophenyl)methyl}-1H-imidazol-5-yl]-2-methyl-2-propenoate (0.85 g, 59%) as an oil; NMR (NOE) was consistent with the structure.

(v)
(E)-3-[2-n-butyl-1-{(2-chlorophenyl)methyl}-1H-imidazol-5-yl]-2-methyl-2-propenoic acid A solution of the ethyl ester (Example 1 (iv)) (850 mg, 2.36 mmol) in ethanol (10 mL) was treated with a solution of sodium hydroxide (283 mg of sodium hydroxide pellets in 2 mL of water) at room temperature for 2 hours. The reaction was acidified in the cold to pH 3.5 with dilute hydrochloric acid solution to deposit a white precipitate. The product was filtered, washed with water and dried at 40° C. for 18 hours to give (E)-3-[2-n-butyl-1-{(2-chlorophenyl)methyl}-1H-imidazol-5-yl]-2-methyl-2-propenoic acid; 539 mg, mp 228°–229° C. The NMR (NOE) supports the trans stereochemistry of the carboxylic acid and imidazole groups.

EXAMPLES 2–10

In Table I are listed other examples of alkenoic acids prepared form 2-n-butyl-1-(2-chlorophenyl)methyl-1H- imidazole-5-carboxaldehyde by the methods described in Example 1 (iv-v). The reagents and products are shown in Table I.

EXAMPLE 11

(E and Z)-3-2-n-Butyl-1-{(2-chlorophenyl)methyl}-1H-imidazol-5-yl]-2-propenoic Acid

Method A

The modification of the procedure of Example 1 (iv-v) was used. To a suspension of sodium hydride (0.492 g, 0.0205 mol) in glyme (30 mL) was added drop-

TABLE I

Alkenoic Acids

| | | | | Products (percentage yield) | |
|---|---|---|---|---|---|
| | | | | (E) $\underset{{}^aIM}{\overset{H}{\diagdown}}C=C\underset{R^1}{\overset{CO_2R}{\diagup}}$ | (Z) $\underset{{}^aIM}{\overset{H}{\diagdown}}C=C\underset{CO_2R}{\overset{R^1}{\diagup}}$ |
| Example | Reactant[b] | R | $R^1$ | | |
| 1 | $(EtO)_2P(O)CH(CH_3)COOEt$ | Et | $CH_3$ | oil (59) | (<5) |
| | | H | $CH_3$ | mp 228–229° C. (69) | — |
| 2 | $(MeO)_2P(O)CH(CH_2C_6H_5)COOMe$[c] | Me | $CH_2C_6H_5$ | oil (42) | oil (14) |
| | | H | $CH_2C_6H_5$ | mp 176.5–178° C. (64) | mp 95–97° C. (78) |
| 3 | $(MeO)_2P(O)CH(CH_2CH_2C_6H_5)COOMe$[d] | Me | $CH_2CH_2C_6H_5$ | oil (14) | — |
| | | H | $CH_2CH_2C_6H_5$ | mp 185.5–190° C. (62) | — |
| 4 | $(EtO)_2POCH(C_4H_9)COOEt$[d] | Et | $C_4H_9$ | oil (49) | oil (14) |
| | | H | $C_4H_9$ | mp 179–181° C. (62) | mp 140–141.5° C. (45) |
| 5 | $(MeO)_2P(O)CH[CH(CH_3)(C_6H_5)]COOMe$[d] | Me | $CH(CH_3)C_6H_5$ | oil (23) | oil (19) |
| | | H | $CH(CH_3)C_6H_5$ | mp 184–186° C. (73) | mp 142–143° C. (35) |
| 6 | $(MeO)_2P(O)CH(CH_2C_6H_4\text{-}p\text{-}OMe)\text{—}COOMe$[d] | Me |  | oil (40) | oil (31) |
| | | H | | mp 158–159.5° C. (73) | — |
| 7 | $(MeO)_2P(O)CH(CH_2\text{-}2\text{-naphthyl})COOMe$[d] | Me | 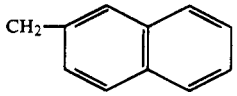 | oil (52) | oil (31) |
| | | H | | mp 164–165° C. | mp 149–150° C. |
| 8 | $(MeO)_2P(O)CH(CH_2\text{—}C_6H_3\text{-}3,4\text{-dichloro})COOMe$[d] | Me | 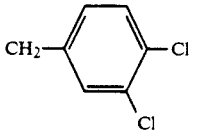 | oil (57) | oil (19) |
| | | H | | mp 177–178° C. (63) | mp 182–183° C. (33) |
| 9 | $(MeO)_2P(O)CH(CH_2\text{—}C_6H_4\text{-}m\text{-}OC_6H_5)COOMe$[d] | Me | 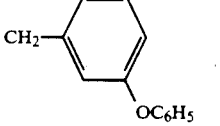 | oil (46) | oil (34) |
| | | H | | mp 164–165° C. (52) | mp 119–120° C. (47) |
| 10 | $(MeO)_2P(O)CH(CH_2\text{—}C_6H_4\text{-}o\text{-}CH_3)COOMe$[d] | Me | 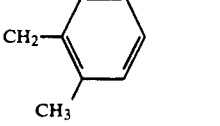 | oil (50) | oil (24) |
| | | H | | mp 190–191° C. (80) | mp 193–195° C. (68) |

${}^aIM =$ 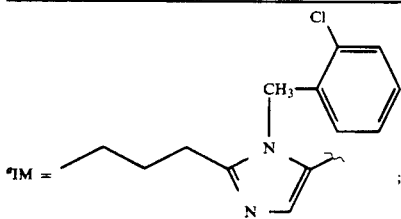 ;

[b]Prepared as in c and d;
[c]Prepared from trimethyphosphonoacetate, benzyl bromide and NaH in glyme at 60° C. followed by flash chromatography to give 77% of trimethyl 3-phenyl-2-phosphonopropionate.
[d]Reactants for 3–10 prepared as in c except the following reagents were used: 2-phenylethyl bromide, butyl bromide, α-bromoethylbenzene, α-chloromethylfuran, p-methoxybenzyl chloride, 2-naphthylmethyl chloride, 3,4-dichlorobenzyl chloride, m-phenoxybenzyl chloride, and 2-methylbenzyl chloride.

wise under argon trimethyl phosphonoacetate (3.73 g, 0.0205 mol). After one hour at ambient temperature, 2-n-butyl-1-(2-chlorophenyl)methyl-1H-imidazol-5-carboxaldehyde (3.78 g, 0.0137 mol) was added, and the mixture was stirred at 40° C. for one hour. The reaction was quenched with ice water, the product extracted into ether and the washed, dried concentrated product slowly crystallized to the low melting solid (3.39 g, 83%) methyl (E)-3-[2-n-butyl-1-{(2-chlorophenyl)methyl}-1H-imidazol-5-yl]-2-propenoate. None of the Z isomer was detected by TLC or NMR in the purified product. The (E) ester (132 mg) was dissolved in ethanol (4 mL) and 10% sodium hydroxide solution (0.5 mL) was added. The solution was stirred at 25° C. under argon for 17 hours, 10% hydrochloric acid solution was added to pH 3.5 and the white solid was filtered, washed with water, and dried at 40° C. in vacuum to give 71 mg (59%) of E-3-[2-n-butyl-1-{(2-chlorophenyl)methyl}-1H-imidazol-5-yl]-2-propenoic acid; mp 178°–179° C.

Method B (i) 2-n-butyl-1-(trimethylsilyl)-ethoxymethylimidazole

Hexane-washed 80% sodium hydride (1.45 g, 0.0483 mol) in dimethylformamide (80 mL) under argon was treated with a solution of 2-n-butylimidazole (5.45 g, 0.0439 mol) in dimethylformamide (14 mL) dropwise at 25° C. and the reaction was stirred an additional hour Then 2-(trimethylsilyl)ethoxymethyl chloride (SEM-Cl) (7.68 g, 0.0461 mol) was added, the mixture was stirred for 18 hours at ambient temperature and then partitioned between ice water and ethyl acetate. The washed, dried, concentrated organic solution was chromatographed over silica gel with 1:1 hexane in ethyl acetate to yield 10.8 g (96%) of 2-n-butyl-1-(trimethylsilyl)ethoxymethylimidazole.

(ii) 2-n-butyl-5-tributyltin-1-(trimethylsilyl)ethoxymethylimidazole

A solution of 2-n-butyl-1-SEM imidazole (prepared above) (6.37 g, 0.025 mol) in ethyl ether (125 mL) was treated dropwise with n-butyl lithium (0.0255 mol, 10.2 mL of 2.5 M in hexane) under argon at room temperature. After being stirred for an additional 45 minutes, tributyltin chloride (8.83 g, 7.4 mL, 0.026 mol) was added dropwise. The suspension was stirred overnight, saturated ammonium chloride solution was added and the ether layer was separated, washed with brine, dried over sodium sulfate, concentrated and flash chromatographed over silica gel with 3:1 hexane/ethyl acetate to provide 11.3 g (83%) of 2-n-butyl-5-tributyltin-1-(trimethylsilyl)-ethoxymethylimidazole.

(iii) ethyl (E and Z)-3-[2-n-butyl-1-{(trimethylsilyl)ethoxymethyl}-1H-imidazol-5-yl]-2-propenoate To a solution of n-butyl-5-tributyltin-1-(trimethylsilyl)ethoxymethylimidazole (11.3 g, 0.0208 mol) in m-xylene (150 mL) was added ethyl 3-bromopropenoate (4.17 g, 0.0233 mol), followed by tetrakis(triphenylphosphine)palladium(0) (0.48 g, 0.416 mmol). The reaction mixture was heated at 120° C. for 18 hours under argon. The cooled mixture was washed with water, 10% ammonium hydroxide solution and brine. The solution was treated with charcoal and sodium sulfate, filtered, concentrated and chromatographed over silica gel with 9:1 hexane in ethyl acetate to give 1.96 g (27%) of ethyl (Z)-3-[2-n-butyl-1-{(trimethylsilyl)ethoxymethyl}-1H-imidazol-5-yl]-2-propenoate as an oil. Further elution with 4:1 hexane acetate afforded the E-isomer (1.98 g, 27%) as an oil.

(iv) ethyl (E and Z)-3-[3-n-butyl-1-t-butoxycarbonyl-1H-imidazol-5-yl]-2-propenoate A solution of ethyl-(Z)-3-[2-n-butyl-1-{(trimethylsilyl)ethoxymethyl}-1H-imidazol-5-yl]-2-propenoate (1 24 g, 3.52 mmol) in ethanol (10 mL) was heated at 60° C. for 3.5 hours with 5N hydrochloric acid solution (20 mL). The cooled reaction was basified with 10% sodium hydroxide solution, extracted with ethyl acetate, washed with water, dried and concentrated to 0.644 g (82%) of an oil. This was dissolved in methanol (15 mL), triethylamine (1.5 mL, 10.6 mmol), and di-tert-butyldicarbonate (2.3 g, 10.5 mmol) were added and the mixture was stirred for 18 hours at ambient temperature. The mixture was concentrated in vacuo and chromatographed over silica gel with 4:1 hexane/ethyl acetate to give 0.402 g (36%) of ethyl (Z)-3-[2-n-butyl-1-t-butoxy-carbonyl-1H-imidazol-4-yl]-2-propenoate as an oil. The (E)-isomer was prepared by the same procedure described for the (Z)-isomer. From 1.02 g (2.9 mmol) of ethyl (E)-3-[2-n-butyl-1-{(trimethylsilyl)ethoxy-methyl}-1H-imidazol-5-yl]-2-propenoate was obtained 334 mg (36%) ethyl (E)-3-[2-n-butyl-1-t-butoxycarbonyl-1H-imidazol-5-yl]-2-propenoate as an oil.

(v) ethyl (E and Z)-3-[2-n-butyl-1-{(2-chlorophenyl)methyl)-1H-imidazol-5-yl]-2-propenoate To a stirred solution of trifluoromethanesulfonic anhydride (387 mg, 1.37 mmol) in methylene chloride (1 mL) held at −75° C. under argon was added a solution of 2-chlorobenzyl alcohol (196 mg, 1.37 mmol) and diisopropylethylamine (177 mg, 1.37 mmol) in methylene chloride (4 mL). After being stirred for 20 minutes at −75° C., a solution of ethyl (Z)-3-[2-n-butyl-1-t-butoxycarbonyl-1H-imidazol-5-yl]-2-propenoate in methylene chloride (2 mL) was added dropwise over 10 minutes and the mixture was stirred overnight at 25° C. A solution of 5% sodium bicarbonate solution was added with stirring and the layers were separated, washed and dried. The reaction mixture was evaporated to dryness, the residue triturated with 1:1 hexane/ethyl acetate, the solid filtered off and the filtrate was concentrated and chromatographed over silica gel with 7:3 hexane/ethyl acetate to provide the title (Z)-isomer (184 mg, 43%) as an oil. The title (E)-isomer was prepared by the same procedure described for the (Z)-isomer. From 334 mg (1.04 mmol) of ethyl (E)-[2-n-butyl-1-t-butoxycarbonyl-1H-imidazol-5-yl]-2-propenoate was obtained 132 mg (37%) of ethyl(E)-3-[2-n-butyl-1-{(2-chlorophenyl)methyl}-1H-imidazol-5-yl]-2-propenoate which was identical in all respects to the product obtained by Method A.

(vi) (Z)-3-[2-n-butyl-1-{(2-chlorophenyl)methyl}-1H-imidazol-5-yl]-2-propenoic acid The title compound was prepared according to the procedure described in Example 11 Method A by using ethyl (Z)-3-[2-n-butyl-1-{(2-chlorophenyl)methyl}-1H-imidazol-5-yl]-2-propenoate in place of methyl (E)-3-[2-n-butyl-1-{(2-chlorophenyl)methyl}-1H-imidazol-5-yl]-

2-propenoate. The title compound had a mp 183°–184° C. The NMR was consistent with a cis or (Z) relationship of the imidazole and carboxyl groups.

EXAMPLE 12

(E)-3-[2-n-Butyl-1{(2-chlorophenyl)methyl}-1H-imidazol-5-yl]-3-methyl-2-propenoic Acid (i)
2-n-butyl-1-(2-chlorophenyl)methyl-5-(α-hydroxy)ethyl-1H-imidazole A solution of 2-n-butyl-1-(2-chlorophenyl)methyl-1H-imidazole-5-carboxaldehyde (Example 1(ii)) (1.1 g, 3.97 mmol) was dissolved in dry tetrahydrofuran (15 mL), cooled to −78° C. under argon and a solution of methyl lithium (3.64 ml of 1.2 M in diethyl ether, 4.57 mmol) was added dropwise. The mixture was stirred for 1.5 hours, quenched with ammonium chloride solution, warmed to ambient temperature and extracted with ethyl acetate. The washed, dried, concentrated product was flash chromatographed over silica gel with ethyl acetate to provide 1.07 g (92%) of 2-n-butyl-1-(2-chlorophenyl)methyl-5-(a-hydroxy)ethyl-1H-imidazol.

(ii)
[2-n-butyl-1-{(2-chlorophenyl)methyl}-1H-imidazol-5-yl]methyl ketone

A mixture of 2-n-butyl-1-(2-chlorophenyl)methyl-5-(a-hydroxy)ethyl-1H-imidazole (1.07 g, 3.65 mmol), activated manganese dioxide (6 g) and toluene (75 mL) was heated at 90° to 100° C. under a slight vacuum with a Dean Stark water separator for 17 hours. The inorganics were filtered, the concentrated filtrate was applied to a flash silica gel column and the product was eluted with 3:7 hexane/ethyl acetate to give 0.628 g (59%) of [2-n-butyl-1-{(2-chlorophenyl)methyl}-1H-imidazol-5-yl]methyl ketone.

(iii) ethyl
(E)-3-[2-n-butyl-1-{(2-chlorophenyl)methyl}-1H-imidazol-5-yl]-3-methyl-2-propenoate To absolute ethanol (3 mL) was added freshly cut sodium (55 mg). Then triethyl phosphonoacetate (0.504 g, 2.16 mmol) and [2-n-butyl-1-{(2-chlorophenyl)methyl}-1H-imidazole-5-yl]methyl ketone (0.628 g, 2.16 mmol) were added and the mixture was stirred at 70° C. for 17 hours. The reaction was concentrated, partitioned between ethyl acetate and water, and the organic layer was washed with water, dried, concentrated and chromatographed to afford 214 mg (27%) of the title compound. The NMR was consistent with a trans relationship of imidazole to the carboxylate group.

(iv)
(E)-3-[2-n-butyl-1-{(2-chlorophenyl)methyl}-1H-imidazol-5-yl]-3-methyl-2-propenoic Acid The title compound was prepared according to Example 1(v) by using ethyl (E)-3-[2-n-butyl-1-{(2-chlorophenyl)methyl}-1H-imidazol-5-yl]-3-methyl-2-propenoate in place of ethyl-(E)-3-[2-n-butyl-1-{(2-chlorgphenyl)methyl}-1H-imidazol-5-yl]-2-methyl-2-propenoate. The title compound was a white solid, and was converted to the hydrochloride salt to give 82 mg (41%); mp 198°–199.5° C. (from ethyl acetate/methanol).

EXAMPLE 13

(E)-3-2-n-Butyl-1-{(2-chloro-6-fluorophenyl)methyl}-1H-imidazol-5-yl]-2-benzyl-2-propenoic Acid (i)
2-n-butyl-1-(2-chloro-6-fluorophenyl)methyl-1H-imidazole A solution of 2-n-butylimidazole (3.75 g, 0.03 mol) in dry dimethylformamide (4 mL) was added to sodium hydride (0.95 g) in dimethylformamide (18 mL). After the gas evolution subsided, the mixture was stirred one hour under argon and 2-chloro-6-fluorobenzylchloride (5.5. g, 0.031 mol) in dimethylformamide (7 mL) was added to produce an exotherm. The mixture was stirred for 17 hours at ambient temperature, diluted with ice water and extracted with ethyl acetate. The washed, dried, concentrated organic layer provided 7.63 (94%) of the title compound whose NMR was consistent with the structure. This material was used without further purification.

(ii)
2-n-butyl-1-(2-chloro-6-fluorophenyl)methyl-1H-imidazol-5-carboxaldehyde

The procedures of Example 1(ii-iii) were used. From 7.63 g of crude 2-n-butyl-1-(2-chloro-6-fluorophenyl)-methyl-1H-imidazole and proportional amounts of other reagents was obtained 2.8 g of 2-n-butyl-1-(2-chloro-6-fluorophenyl)methyl-5-hydroxymethyl-1H-imidazole after chromatography over silica gel with 3% of methanol in methylene chloride; mp 106°–108° C. (from ethyl acetate). This material was oxidized with manganese dioxide and worked up as described above to give 0.88 g (63%) of 2-n-butyl-2-(2-chloro-6-fluorophenyl)methyl-1H-imidazol-5-carboxaldehyde; mp 88°–90° C. (from ethyl acetate).

(iii)
(E)-3-[2-n-butyl-1-{(2-chloro-6-fluorophenyl)methyl}-1H-imidazol-5-yl]-2-benzyl-2-propenoic acid The procedure of Example 1(iv-v) was used. From 0.9 g (3.05 mmol) of 2-n-butyl-1-(2-chloro-6-fluorophenyl)-methyl-1H-imidazol-5-carboxaldehyde, 3 g (11 mol) of trimethyl benzylphosphonoacetate, 0.28 g of sodium hydride and glyme (12 mL) held at 60° C. for 1 hour was obtained, after chromatography over silica gel with 50% of hexane in ethyl acetate, 0.44 g (33%) of the trans isomer methyl (E)-[2-n-butyl-1-{(2-chloro-6-fluorophenyl)methyl} -1H-imidazol-5-yl]-2-benzyl-2-propenoate and 0.01 g (8%) of the corresponding cis or (Z)-isomer. The (E)-isomer(0.43 g, 0.98 mmol) was hydrolyzed to the acid and the product was crystallized from methanol to afford 0.38 g (91%) of (E)-3-[2-n-butyl-1-{(2-chloro-6-fluorophenyl)methyl}-1H-imidazol-5-yl]-2-benzyl-2-propenoic acid; mp 204°–206° C.

EXAMPLE 14

(E)-3-[2-n-Butyl-1-{(2-chlorophenyl)methyl}-1H-imidazol-5-yl]-2-phenyl-2-propenoic Acid A mixture of 2-n-butyl-1-(2-chlorophenyl)methyl-1H-imidazole-5-carboxaldehyde (554 mg, 2 mmol), phenylacetic acid (310 mg, 2.3 mmol), potassium carbonate (126 mg, 0.91 mmol), and acetic anhydride (1 mL) was heated gradually to 140° C. and held at this temperature for 6 hours. The cooled reaction was diluted with water and the oily solid was separated, triturated several times with ether, and the solid was crystallized several times from methanol/ethyl acetate to give 143 mg (18%) of the title compound; mp 210°-212° C. The NMR was consistent with the trans olefinic product.

EXAMPLE 15

(E)-3-[2-n-Butyl-1-{(2-chlorophenyl)methyl}-1H-imidazol-5-yl]-2-(2-naphthyl)-2-propenoic Acid The compound was prepared according to Example 14 using 2-naphthylacetic acid in place of phenylacetic acid. The title compound was a solid; mp 271°-273° C. (d).

EXAMPLE 16

(E)-3-[2-n-Butyl-1-{(2-chlorophenyl)methyl}-1H-imidazol-5-yl]-2-heptenoic Acid (i) Ethyl 3-trifluoromethane-sulfonyloxy-2-heptenoate Ethyl 3-ketoheptanoate (2.07 g, 12 mmol) was dissolved in dimethylformamide (60 mL) under argon and sodium hydride (357 mg, 14.4 mmol) was added. After 30 minutes at room temperature the solid N-phenyltrifluoromethanesulfonimide (*Tetra. Letters*, (1983), 24, 979) (4.97 g, 13.8 mmol) was added. The reaction was stirred for 2 hours, diluted with ether/water and the usual workup gave after chromatography with 5:95 ether/hexane 3.45 g (94%) of ethyl 3-trifluoromethanesulfonyloxy-2-heptenoate.

(ii) ethyl (E)-3-[2-n-butyl-1-{(trimethylsilyl)ethoxymethyl}-1H-imidazol-5-yl]-2-heptenoate A solution of 2-n-butyl-5-tributyltin-1-(trimethylsilyl)ethoxymethyl imidazole (Example 11, Method B(ii)) (1.973 g, 3.63 mmol) and ethyl 3-trifluoromethanesulfonyloxy-2-heptenoate (1.1 g, 3.62 mmol) in tetrahydrofuran (5 mL) was added to a mixture of lithium chloride (4.70 mg, 11.1 mmol) and tetrakis(triphenylphosphine)-palladium(O) (88 mg, 0.076 mmol) in tetrahydrofuran (10 mL). The reaction was heated to reflux under argon for 5 hours, cooled, diluted with ether and the ether layer was washed with water, 10% ammonium hydroxide solution and brine The extract was dried with sodium sulfate and concentrated. The crude product (2.58 g) was chromatographed over silica gel with a gradient of hexane in ethyl acetate to give 1.09 g (74%) of the title compound (iii) ethyl (E)-3-[2-n-butyl-1-{(2-chlorophenyl)methyl}-1H-imidazol-5-yl]-2-heptenoate The procedure of Example 11, Method B(iv, v) was followed using ethyl (E)-3-[2-n-butyl-1-{(trimethylsilyl)ethoxymethyl}-1H-imidazol-5-yl]-2-heptenoate in place of ethyl (E)-3-[2-n-butyl-1-{(trimethylsilyl)ethoxymethyl}-1H-imidazol-5-yl]-2-propenoate. The title compound was isolated as an oil after this three step reaction sequence in a yield of 40% after chromatography.

(iv) (E)-3-[2-n-butyl-1-{(2-chlorophenyl)methyl}-1H-imidazol-5-yl]-2-heptenoic acid The ethyl ester (149 mg) was dissolved in ethanol (2 mL) and 10% sodium hydroxide solution (0.5 mL) was added. An additional 1 ml of base was added incrementally over several hours and the mixture was stirred overnight at room temperature. The cooled reaction was acidified to pH 5 with dilute hydrochloric acid solution, extracted with methylene chloride and the resulting residue was triturated with ether/hexane to provide 56 mg of the title compound; mp 131°-132° C.

EXAMPLE 17

(E)-3-2-n-Butyl-1-{(2-chlorophenyl)methyl}-1H-imidazol-5-yl]-4-phenyl-2-butenoic Acid (i) Ethyl 4-phenyl-3-trifluoro-methanesulfonyloxy-2-butenoate This compound was prepared according to Example 16(i) using ethyl 4-phenyl-3-ketobutanoate in place of ethyl 3-ketoheptanoate.

(ii) ethyl (E)-3-[2-n-butyl-1-{(trimethylsilyl)ethoxymethyl}-1H-imidazol-5-yl]-4-phenyl-2-butenoate To a solution of 2-n-butyl-1-SEM-imidazole (Example 11, Method B(i)) (1.8 g, 5.32 mmol) in ethyl ether (16 mL) was added n-butyl lithium in hexane (6.5 mmol) at a slow rate. After an additional hour of stirring at 25° C., a solution of zinc chloride in ether (6.5 mL of 1.0 M) was added followed by tetrahydrofuran (15 mL). After an additional 75 minutes of stirring, the zinc chloride imidazole adduct solution was transferred under argon to a solution of ethyl 4-phenyl-3-trifluoromethanesulfonyloxybutenoate (1.63 g, 6.41 mmol) and tetrakis(triphenylphosphine)palladium(O) (317 mg) in tetrahydrofuran (30 mL). The reaction mixture was stirred at 25° C. for 20 hours and worked up as in Example 16(ii) to provide 1.77 g (75%) of ethyl (E)-3-[2-n-butyl-1-(trimethylsilyl)ethoxymethyl}-1H-imidazol-5-yl]-4-phenyl-2-butenoate.

(iii) ethyl (E)-3-[2-n-butyl-1-{(2-chlorophenyl)methyl}-1H-imidazol-5-yl]-4-phenyl-2-butenoate The compound was prepared according to the procedure of Example 11, Method B(iv, v) using ethyl (E)-3-[2-n-butyl-1-((trimethylsilyl)ethoxymethyl}-1H-imidazol-5-yl]-4-phenyl-2-butenoate in place of ethyl (E)-3-[2-n-butyl-1-{(trimethylsilyl)ethoxymethyl}-1H-imidazol-5-yl]-2-propenoate. The title compound was an oil.

(iv) (E)-3-[2-n-butyl-1-{(2-chlorophenyl)methyl}-1H-imidazol-5-yl]-4-phenyl-2-butenoic acid The above ethyl ester (520 mg) was dissolved in ethanol (5 mL) and 5 N hydrochloric acid solution (40 mL), and the solution was slowly heated at 100° C. with evaporation of the alcohol. After being heated at 100° C. for 6 hours, the reaction was cooled and the white precipitate was collected, air-dried, and then triturated with ether/methanol to afford 345 mg (65%) of (E)-3-[2-n-butyl-1-{(2-chlorophenyl)methyl}-1H-imidazol-5-yl]-4-phenyl-2-butenoic acid hydrochloride; mp 92°-94° C.

EXAMPLE 18

(E)-4-[2-n-Butyl-1-{(2-chlorophenyl)methyl}-1H-imidazol-5-yl]-3-butenoic Acid (i)
(E)-3-[2-n-butyl-1-{(2-chlorophenyl)methyl}-1H-imidazol-5-yl]-2-propenol A solution of methyl (E)-3-[2-n-butyl-1-{(2-chlorophenyl)methyl}-1H-imidazol-5-yl]-2-propenoate (Example 11, Method A) (0.5 g, 1.5 mmol) in dry tetrahydrofuran (10 mL) held at −78° C. under argon was treated dropwise with a solution of diisobutyl aluminum hydride in toluene (3.30 mmol, 2.2 mL of 1.5 M). The mixture was allowed to warm to ambient temperature and stirred an additional 17 hours. Excess reducing agent was quenched with methanol and water, dilute acetic acid and methylene chloride were added, and the organic layer was washed with sodium bicarbonate solution, dried and concentrated to 0.507 g of the title compound as an oil.

(ii) ethyl
(E)-3-[2-n-butyl-1-{(2-chlorophenyl)methyl}-1H-imidazol-5-yl]-2-propenyl carbonate To a solution of (E)-3-[2-n-butyl-1-{(2-chlorophenyl)methyl}-1H-imidazol-5-yl]-2-propenol (2.09 g, 6.86 mmol) in methylene chloride (20 mL) and triethylamine (1.25 mL, 12.4 mmol) cooled to 0° C. under argon was added dropwise ethyl chloroformate (1.34 g, 1.18 ml, 12 mmol). The reaction was then stirred at ambient temperature overnight. Ethyl acetate was added, the precipitate filtered and the concentrated filtrate was flash chromatographed over silica gel with 3:7 hexane/ethyl acetate to provide 1.67 g (65%) yield of the title carbonate as an oil. The NMR and IR of the product were consistent with the structure.

(iii) ethyl
(E)-4-[2-n-butyl-1-{(2-chlorophenyl)methyl}-1H-imidazole-5-yl]-3-butenoate A solution of ethyl (E)-3-[2-n-butyl-1-{(2-chlorophenyl)methyl}-1H-imidazol-5-yl]-2-propenyl carbonate (1.42 g, 3.77 mmol) in tetrahydrofuran (12 mL) under an atmosphere of carbon monoxide was treated with triphenylphosphine (49 mg, 0.188 mmol) and palladium diacetate and the mixture was heated at 40° C. for 2½ hours. The concentrated reaction mixture was applied to a flash column of silica gel and eluted with 1:1 hexane/ethyl acetate to afford 355 mg (26%) of the title compound as an oil.

(iv)
(E)-4-[2-n-butyl-1-{(2-chlorophenyl)methyl}-1H-imidazol-5-yl]}-3-butenoic acid The compound was prepared according to the procedure of Example 1(v) using ethyl (E)-4-[2-n-butyl-1-{(2-chlorophenyl)methyl}-1H-imidazol-5-yl]-3-butenoate in place of ethyl (E)-3-[2-n-butyl-1-{(2-chlorophenyl)methyl}-1H-imidazol-5-yl]-2-methyl-2-propenoate. The title compound is a white solid; mp 135°–137° C., hydrochloride salt; mp 176°–178° C.

EXAMPLE 19

(E)-4-2-n-Butyl-1-{(2-chloroohenyl)methyl}-1H-imidazol-5-yl]-2,2-bis(benzyl)-3-butenoic Acid (i) ethyl
(E)-4-[2-n-butyl-1-{(2-chlorophenyl)methyl}-1H-imidazol-5-yl]-2,2-bis(benzyl)-3-butenoate A solution of ethyl (E)-4-[2-n-butyl-1-{(2-chlorophenyl)methyl}-1H-imidazol-5-yl]-3-butenoate (256 mg, 0.709 mmol) in tetrahydrofuran (5 mL) was cooled to −78° C. under argon, and lithium diisopropylamide (0.85 mmol, 1 M in tetrahydrofuran) was added. After 10 minutes benzyl bromide (243 mg, 1.42 mmol) was added. The mixture was then stirred at room temperature overnight, diluted with 10% ammonium chloride and extracted with ethyl acetate. The dried, concentrated product was chromatographed over silica gel with 6:4 hexane/ethyl acetate to give 128 mg (33%) of the title compound as an oil. NMR indicated the bis(-benzyl) substitution.

(ii)
(E)-4-[2-n-butyl-1-{(2-chlorophenyl)methyl}-1H-imidazol-5-yl]-2,2-bis(benzyl)-3-butenoic acid A solution of ethyl (E)-4-[2-n-butyl-1-{(2-chlorophenyl)methyl}-1H-imidazol-5-yl]-2,2-bis(benzyl)-3-butenoate (121 mg) in ethanol (5 mL) was heated to reflux with 10% sodium hydroxide solution (3 mL) for 2 hours. The ethanol was evaporated, water was added and the aqueous layer was extracted with ether. The water layer was acidified to pH 1 with dilute hydrochloric acid solution, extracted with ethyl acetate, dried and concentrated to a solid. Trituration with ether provided 75 mg of the white solid hydrochloride salt of the title compound; mp 184°–185° C.

EXAMPLE 20

(E)-4-[2-n-Butyl-1-{(2-chlorophenyl)methyl}-1H-imidazol-5-yl]-2methyland -2,2-dimethyl)-3-butenoic Acid These compounds are prepared according to the procedure of Example 19(i,ii) using one or two equivalents of methyl iodide in place of benzyl bromide.

EXAMPLE 21

(E)-4-2-n-Butyl-1-((2-chlorophenyl)methyl)-1H-imidazol-5-yl11-2-benzyl-3-butenoic Acid This compound is prepared according to Example 19(i,ii) but using less than one equivalent of benzyl bromide at higher solvent dilution.

EXAMPLE 22

(E,E)-5-[2-n-Butyl-1-{(2--chlorophenyl)methyl}-1H-imidazol-5-yl1-2,4-pentadienoic Acid (i) ethyl
(E,E)-5-[2-n-butyl-1-{(2-chlorophenyl)methyl}-1H-imidazol-5-yl]-2,4-pentadienoate This compound was prepared according to the procedure of Example 1(iv). From 0.83 g (3 mmol) of 2-n-butyl-1-(2-chlorophenyl)methyl-1H-imidazol-5-carboxaldehyde, 0.78 g (3.75 mmol) of triethyl 4-phosphonocrotonate, 0.108 g (4.5 mmol) of sodium hydride and 10 mL of glyme was obtained after flash chromatography 511 mg (38%) of the low melting solid ethyl (E,E)-5-[2- n-butyl-1-{(2-chlorophenyl)methyl}-1H-imidazol-5-yl]-2,4-pentadienoate.

(ii) (E,E)-5-[2-n-butyl-1-{(2-chlorophenyl)methyl}-1H-imidazol-5-yl]-2,4-pentadienoic acid This compound was prepared according to the procedure of Example 1(v) using ethyl (E,E)-5-[2-n-butyl-1-{(2-chlorophenyl)methyl}-1H-imidazol-5-yl]-2,4-pentadienoate in place of ethyl (E)-3-[2-n-butyl-1-{(2-chlorophenyl)methyl} -1H-imidazol-5-yl]-2-methyl-2-propenoate. The title compound was a white solid, obtained in 75% yield; mp 219°-220° C.

EXAMPLE 23
(E)-3-2-n-Butyl-1-{(2-chlorophenyl)methyl}-1H-imidazol-5-yl-2-benzyl-2-butenoic Acid (i) Ethyl 2-benzyl-3-trifluoro-methanesulfonyloxy-2-butenoate This compound was prepared according to the procedure of Example 16(i) using ethyl 2-benzyl-acetoacetate in place of ethyl 3-ketoheptanoate. The title compound was obtained in 86% yield and NMR (NOE) showed one isomer in a trans relationship of benzylic to methyl groups.

(ii) ethyl (E)-3-[2-n-butyl-1-{(trimethylsilyl)ethoxymethyl}-1H-imidazol-5-yl]-2-benzyl-2-butenoate This compound was prepared according to the procedure of Example 16(ii) by using ethyl 2-benzyl-3-trifluoromethanesulfonyloxy-2-butenoate in place of ethyl 3-trifluoromethanesulfonyloxy-2-heptenoate. The title compound was obtained in 28% yield and is an oil.

(iii) ethyl (E)-3-[2-n-butyl-1-{(2-chlorophenyl)methyl}-1H-imidazol-5-yl]-2-benzyl-2-butenoate The procedure of Example 11, Method B(iv,v) was followed using ethyl (E)-3-[2-n-butyl-1-{(trimethyl silyl)-ethoxymethyl}-1H-imidazol-5-yl]-2-benzyl-2-butenoate in place of benzyl(E)-3-[2-n-butyl-1-{(trimethylsilyl)-ethoxymethyl}-1H-imidazol-5-yl]-2-propenoate. The title compound was obtained in 57% overall yield from the SEM-derivative.

(IV) (E)-3-[2-n-butyl-1-{(2-chlorophenyl)methyl}-1H-imidazol-5-yl]-2-benzyl-2-butenoic acid A solution of ethyl (E)-3-[2-n-butyl-1-{(2-chlorophenyl)methyl}-1H-imidazol-5-yl]-2-benzyl-2-butenoate (623 mg, 1.38 mmol) in ethanol (25 mL) under argon was treated with 10% sodium hydroxide solution (20 mL), and then stirred for 1 hour at room temperature. An additional 25 mL of 10% sodium hydroxide were added and the mixture was stirred overnight at ambient temperature. Acidification to pH 4 with dilute hydrochloric acid solution followed by extraction with methylene chloride and washing with water gave after drying and workup, 630 mg of crude product. Trituration with ethyl acetate/ether provided the title compound (302 mg, 52%), mp 206°-207° C., as the white hydrochloride salt.

EXAMPLE 24
2n-Butyl-1[(2-chlorophenyl)methyl]-}-methylene-a-benzyl)-1H-imidazole-5-propanoic Acid A solution of (Z)-3-[2-n-butyl-1-{(2-chlorophenyl)methyl}-1H-imidazol-5-yl]-2-benzyl-2-butenoic acid (200 mg) in ethanol (15 mL) was treated with sodium hydroxide solution. The crude product was triturated with methanol/ether to provide 0.115 g of the deconjugated acid, 2-n-butyl-1-[(2-chlorophenyl)methyl]-β-methylene-α-(benzyl)-1H-imidazole-5-propanoic acid; mp 169°-171° C.

EXAMPLE 25
(E)-3-[2-n-Butyl-1-{(2-chloropheny)methyl}-1H-imidazol-5-yl]-2-(benzyl)-2-propenoic Acid, 2-(N,N-Diethylamino)-2-oxoethyl Ester A solution of (E)-3-[2-n-butyl-1-{(2-chlorophenyl)methyl}-1H-imidazol-5-yl]-2-(benzyl)-2-propenoic acid (Example 2) (2.05 g, 5 mmol) in dry dimethylformamide (10 mL) was treated with 2-chloro-N,N-diethylacetamide (0.825 g, 5.51 mmol) followed by powdered potassium carbonate. This mixture was heated at 70° C. for 7 hours, diluted with water and extracted with ethyl acetate. The water-washed, dried, concentrated product solidified and after trituration with ether/hexane afforded 2.04 g (78%) of the title ester; mp 76°-77° C.

EXAMPLE 26
(E)-3-2-n-Butyl-1-{(2-chlorophenyl)methyl}-4-hydroxymethyl-1H-imidaol-5yl]-2benzyl-2-propenoic acid (i) 2-n-butyl-1-(2-chlorophenyl)methyl-4-(t-butyldimethylsilyloxy)methyl-1H-imidazol-5-carboxaldehyde A solution of 2-n-butyl-1-(2-chlorophenyl)methyl-4,5-bis(hydroxy)methyl-1H-imidazole (Example 1(ii)) (310 mg, 1 mmol) in methylene chloride (5 mL) was treated with 4-dimethylaminopyridine (5.2 mg), triethylamine (1.5 mmol) and t-butyl dimethylsilyl chloride (192 mg, 1.24 mmol). The mixture was stirred at 25° C. for 20 hours, diluted with water and the organic layer was washed well with water, dried, concentrated and chromatographed over silica gel with an ethyl acetate/methanol gradient to afford 127 mg (24%) of the bis (4,5-t-butyldimethylsilyl) ether and 252 mg (59%) of 2-n-butyl-1-(2-chlorophenyl)methyl-4-t-butyldimethylsilyloxymethyl-5-hydroxymethyl-1H-imidazole. This monoether (252 mg) was oxidized to the 5-carboxaldehyde, using manganese dioxide as described in Example 1(iii) to provide 170 mg of 2-n-butyl-1-(2-chlorophenyl)methyl-4-(t-butyldimethylsilyloxy)methyl- 1H-imidazol-5-carboxaldehyde as an oil.

(ii) ethyl (E)-3-[2-n-butyl-1-{(2-chlorophenyl)methyl}-4-(t-butyldimethylsilyloxy)methyl-1H-imidazol-5-yl]-2-benzyl-2-propenoate In tetrahydrofuran (80 mL) was added n-butyl lithium (15.5 mmol in hexane) and at -78° C. under argon was then added diisopropylamine (2.4 mL, 17.1 mmol). Ethyl 3-phenylpropanoate (2.7 mL, 15.3 mmol) was added neat over 5-6 minutes, and the mixture was stirred an additional 30 minutes at −78° C. A solution of 2-n-butyl-1-(2-chlorophenylmethyl-4-(t-butyldimethylsilyloxy)methyl-1H-imidazol-5-carboxaldehyde (4.29 g, 10.2 mmol) in tetrahydrofuran (10 mL) was added via a cannula, and the reaction mixture was stirred for 15 minutes. The reaction was partitioned between saturated ammonium chloride and ether, and the ether layer was washed with water, dried and concentrated to 7.4 g of crude product. This was chromatographed over silica gel with 20-50% of ethyl acetate in hexane to afford 5.52 g (90%) of a mixture of isomeric β-hydroxy-ester products. A solution of 5.12 g (8.54 mmol) of this mixture in methylene chloride (100 mL) was treated with 4-dimethylaminopyridine (371 mg, 3 mmol) followed by acetic anhydride (8 mL, 84 mmol), and the solution was stirred at room temperature for 5 hours. The reaction was poured into water, stirred for 20 minutes and the product was extracted into ether. The ether extracts were washed with dilute hydrochloric acid solution, water, sodium bicarbonate solution and brine. The dried, concentrated mixture of β-acetoxyester products was used directly in the elimination reaction. To a solution of 2.9 g (4.5 mmol) of the β-acetoxyester product in toluene (60 mL) was added 1.7 mL (10.9 mmol) of 1,8-diazabicyclo[5.4.0]undec-7-ene (DBU), and the mixture was heated at 90° C. for 24 hours. The reaction was concentrated to 10 mL, diluted with ether and flash filtered through a 14×3 cm plug of silica gel with ether rinses to afford 2.6 g (99%) of ethyl (E)-3-[2-n-butyl-1-{(2-chlorophenyl)methyl}-4-t-butyl-dimethyl-silyloxymethyl-1H-imidazol-5-yl]-2-benzyl-2-propenoate. The elimination of the acetate with DBU produced predominately the trans (E) isomer.

(iii)
(E)-3-[2-n-butyl-1-{(2-chlorophenyl)methyl}-4-hydroxymethyl-1H-imidazol-5-yl]-2-benzyl-2-propenoic acid A solution of ethyl (E)-3-[2-n-butyl-1-{(2-chlorophenyl)methyl}-4-t-butyldimethylsilyloxymethyl-1H-imidazol-5-yl]-2-benzyl-2-propenoate (167 mg,. 0.287 mmol) in absolute ethanol (3 mL) was treated portionwise at 6 hour intervals with 10% sodium hydroxide solution (3×1 mL). After being stirred overnight at 25° C., the reaction was heated to 50° C. for 4 hours, then concentrated in vacuo. The residual product was take0 up in water, acidified to pH 5-6 and extracted with methylene chloride. The isolated, dried, concentrated product was triturated with methanol/ether to provide 78 mg (62%) of the title compound; mp 176°-179° C. (d).

EXAMPLE 27

(E)-3-[2-n-Butyl-1-{(2-chlorophenyl)methyl}-1H-imidazol-5-yl]-2-(3,4-methylenedioxyphenyl)methyl-2-propenoic Acid (i)
methyl-3-[2-n-butyl-1-(2-chlorophenyl)methyl-1H-imidazol-5-yl]-3-hydroxy-2-(3,4-methylenedioxyphenyl)methylpropanoate In tetrahydrofuran (20 mL) was placed diisopropylamine (1.41 mL, 10.0 mmol). The mixture was cooled to 0° C. under argon and in n-butyl lithium (4 mL of 2.5 M in toluene, 10.08 mmol) was added. The reaction was stirred at 0° C. for 0.5 hour, then cooled to −78° C. A solution of methyl 3-(3,4-methylenedioxyphenyl)-propanoate (2 g, 9.6 mmol) (prepared by reaction of 3,4-methylenedioxybenzaldehyde with trimethyl phosphonoacetate in the presence of sodium hydride in ethylene glycol dimethyl ether, followed by catalytic hydrogenation with 10% palladium on carbon at 3 atmospheres of hydrogen in an ethyl acetate solution) in tetrahydrofuran (15 mL) was added, and the mixture was stirred at −78° C. for 1 hour. A solution of 2-n-butyl-1-(2-chlorophenyl)methyl-1H-imidazol-5-carboxaldehyde (2.49 g, 9 mmol) in tetrahydrofuran was added, and the mixture was stirred for 30 minutes at −78° C. The reaction was quenched with ammonium chloride solution, and the product was extracted into ethyl acetate. The concentrated product was flash chromatographed with 6:4 ethyl acetate/hexane to yield 1.33 g (31%) of the title compound as an oil.

(ii) methyl
3-acetoxy-3-[2-n-butyl-1-(2-chlorophenyl)methyl-1H-imidazol-5-yl]-2-(3,4-methylenedioxyphenyl)methylpropanoate A solution of methyl 3-[2-n-butyl-1-1(2-chlorophenyl)methyl-1H-imidazol-5-yl]-3-hydroxy-2-(3,4-methlyene-dioxyphenyl)methylpropanoate (1.33 g, 2.7 mmol) in methylene chloride (20 mL) was treated with 4-dimethyl-aminopyridine (91 mg, 0.9 mmol) and acetic anhydride (2.5 mL), and the mixture was stirred for 4 hours at 25° C. Water (5 mL) was added, the mixture was stirred for 1 hour, diluted with sodium bicarbonate solution and the organic layer was washed with water, dried and concentrated to 1.36 g (96%) of the title acetoxy derivative as an oil.

(iii) methyl
(E)-3-[2-n-butyl-1-{(2-chlorophenyl)methyl}-1H-imidazol-5-yl]-2-(3,4-methylenedioxyphenyl)methyl-2-propenoate A solution of methyl 3-acetoxy-3-[2-n-butyl-1-(2-chlorophenyl)methyl-1H-imidazol-5-yl]-2-(3,4-methylenedioxyphenyl)methylpropanoate (1.36 g, 2.58 mmol), 1,8-diazobicyclo[5,4,0]undec-7-ene (1 mL, 6.48 mmol) and toluene (10 mL) was heated at 90° C. for 18 hours under argon. The cooled reaction mixture was diluted with ether, the solution was filtered and the filtrate was concentrated. Chromatography of the product over silica gel with a gradient of ethyl acetate in hexane provided 1.1 g (87%) of methyl (E)-3-[2-n-butyl-1-{(2-chlorophenyl)methyl}-1H-imidazol-5yl]-2-(3,4-methylenedioxyphenyl)methyl-2-propenoate as a low melting solid whose NMR showed the E or trans relationship of the ester group to the imidazole ring.

(iv)
(E)-3-[2-n-butyl-1-{(2-chlorophenyl)methyl}-1H-imidazol-5-yl]-2-(3,4-methylene-dioxyphenyl)methyl-2-propenoic acid The title compound was prepared by the methods described above, by aqueous basic hydrolysis of the ester to provide from 1.1 g of the ester, 0.6 g (51%), m.p. 160°-165° C.

EXAMPLES 28-31

In Table II are listed other examples of alkenoic acids prepared by the methods described in Example 27 (i-iv). The starting materials and products are shown in Table II.

TABLE II

| Example | Starting Materials | | R[3] | Product (R[5])[a] | mp |
|---|---|---|---|---|---|
| 28 | [3-chlorobenzyl-N-pentyl imine with CHO] (II) | 3,4-methylenedioxybenzyl-CH₂CH₂COOMe | H | 3,4-methylenedioxybenzyl-CH₂ | 162–165° C.[b] |
| 29 | (II) | 3,4-methylenedioxy-5-methoxybenzyl-CH₂CH₂COOMe | H | 3,4-methylenedioxy-5-methoxybenzyl-CH₂ | 166–167° C. |
| 30 | (II) | 4-[(CH₂)₂CSi(CH₂)₂O]phenyl-CH₂CH₂COOMe | H | 4-hydroxybenzyl-CH₂ | 255° C. (dec.) |
| 31 | [3-chlorobenzyl-N-pentyl imine with CHO and Cl] | benzyl-CH₂CH₂COOMe | Cl | benzyl-CH₂ | 168–169° C. |

[a] Product prepared by the 4 step synthetic route described in Example 27. The penultimate olefinic ester is purified, if necessary, by chromatography over silica gel with ethyl acetate/hexanes or methanol/ethyl acetate mixtures.
[b] Hydrochloride salt

EXAMPLE 32

(E)-3-[2-n-Butyl-1-{(chlorophenyl))methyl-4-fluoro-1H-imidazol-5-yl]-2-benzyl-2-propenoic Acid By the procedure of Example 29 (i–iv) using 2-n-butyl-1-(2-chlorophenyl)methyl-4-fluoro-1H-imidazol-5-carboxaldehyde and methyl 3-(benzyl)propanoate as the starting materials, the title compound is prepared.

The sodium salt of the acid is isolated from the basic (10% sodium hydroxide) reaction mixture prior to neutralization with dilute acid. The crude reaction solution is applied to a reverse-phase flash column equilibrated with water. The inorganics are washed from the column with water (3 void volumes) and then the product is eluted with a 50:50 mixture of acetonitrile in water. The acetonitrile is removed in vacuo and then the desired sodium salt is obtained after lyophilization.

EXAMPLE 33

(E)-3-[2-n-Butyl-1-{(2-chlorophenyl)methyl}-4-bromo-1H-imidazol-5-yl1-2-benzyl-2-propenoic Acid By the procedure of Example 34 using the corresponding 4-bromo starting material, the title compound is prepared.

EXAMPLE 34

(E)-3-[2-n-Butyl-1-{(2-chlorophenyl)methyl}-4-trifluoromethyl-1H-imidazol-5-yl-2-(3,4-methylenedioxy-phenyl)methyl-2-propenoic Acid Using 2-n-butyl-1-(2-chlorophenyl)methyl-4-trifluoroethyl-1H-imidazol-5-carboxaldehyde (prepared by treating the corresponding 4-bromo compound with trifluoromethyl iodide and copper) in the procedure of Example 27 gives the title compound.

EXAMPLE 35

By the procedure of Example 1, using in place of 2-chlorobenzyl bromide, the following:
2-methylbenzyl bromide,
3-methoxybenzyl bromide,
4-phenylbenzyl bromide, and
4-methoxy-3-methylbenzyl bromide;
and using the phosphonopropionate of Example 6, (MeO)$_2$P(O)CH(CH$_2$C$_6$H$_4$-p-OMe)—COOMe, the following products are obtained:
(E)-3-[2-n-butyl-1-{(2-methylphenyl)methyl}-1H-imidazol-5-yl]-2-(4-methoxyphenyl)methyl-2-propenoic acid,
(E)-3-[2-n-butyl-1-{(3-methoxyphenyl)methyl}-1H-imidazol-5-yl]-2-(4-methoxyphenyl)methyl-2-propenoic acid,
(E)-3-[2-n-butyl-1-{(4-phenylphenyl)methyl}-1H-imidazol-5-yl]-2-(4-methoxyphenyl)methyl-2-propenoic acid, and
(E)-3-[2-n-butyl-1-[(4-methoxy-3-methylphenyl)methyl]-1H-imidazol-5-yl]-2-(4-methoxyphenyl)methyl-2-propenoic acid.

EXAMPLE 36

By the procedure of Example 1, using in place of 2-chlorobenzyl bromide, the following:
4-methoxybenzyl bromide, and
4-methoxy-3-methylbenzyl bromide
and using the phosphonopropionate of Example 2, (MeO$_2$P(O)CH(CH$_2$C$_6$H$_5$)COOMe, the following products are obtained:

(E)-3-[2-n-butyl-1-{(4-methoxyphenyl)methyl}-1H-imidazol-5-yl]-2-benzyl-2-propenoic acid, and
(E)-3-[2-n-butyl-1-{(4-methoxy-3-methylphenyl)methyl}-1H-imidazol-5-yl]-2-benzyl-2-propenoic acid.

EXAMPLE 37

(E)-3-[2-(1-Butenyl)-1-{(2-chlorophenyl)methyl}-1H-imidazol-5-yl]-2-(3,4-dimethoxy-phenyl)methyl-2-propenoic Acid A mixture of 2-n-butyl-1-(2-chlorophenyl)methyl-1H-imidazol-5-carboxaldehyde and N-bromosuccinimide in carbon tetrachloride is irradiated to give the 2-(1-bromobutyl)-imidazole which is dehydrobrominated by treating 1,8-diaza-bicyclo[4.5.0]undec-1-ene in tetrahydrofuran to give 2-(1-butenyl)-1-(2-chlorophenyl)methyl-1H-imidazol-5-carboxaldehyde.

Using the above prepared intermediate and the phosphonopropionate of Example 6 in the procedure of Example 1 gives the title compound.

EXAMPLE 38

(E)-3-[2-Phenyl-1-{(2-chlorophenyl)methyl}-1H-imidazol-5-yl-2-(3,4-dimethoxy-phenyl)methyl-2-propenoic Acid By the procedure of Example 1(ii) Method B, using benzamidine methyl ether in place of valeramidine methyl ether, 2-phenyl-5-hydroxymethylimidazole is prepared and converted to 2-phenyl-1-(2-chlorophenyl)methyl-5-hydroxymethyl-1H-imidazole. The 5-hydroxymethyl group is oxidized using manganese dioxide by the procedure of Example 1 (iii). The resulting 2-phenyl-1-(2-chlorophenyl)methyl-1H-imidazol-5-carboxaldehyde is used in the procedure of Example 27 with methyl 3-(3,4-dimethoxyphenyl)propanoate to give the title compound.

EXAMPLE 39

By the procedure of Example 38 using the following amidine methyl ethers:
C$_{10}$H$_{21}$C=NH(OCH$_3$) and
C$_2$H$_5$C=NH(OCH$_3$);
the following products are obtained:
(E)-3-[2-decyl-1-{(2-chlorophenyl)methyl}-1H-imidazol-5-yl]-2-(3,4-dimethoxyphenyl)methyl-2-propenoic acid and
(E)-3-[2-ethyl-1-{(2-chlorophenyl)methyl}-1H-imidazol-5-yl]-2-(3,4-dimethoxyphenyl)methyl-2-propenoic acid.

EXAMPLE 40

(E)-3-[2-n-Butyl-1-{(2-chlorophenyl)methyl-4-formyl-1H-imidazol-5-yl}-2-benzyl-2-propenoic Acid The title compound was prepared i0 two steps from the dilute HCl hydrolysis of the 4-t-butyl-dimethylsilyloxy group of ethyl 3-[2-n-butyl-1-{(2-chlorophenyl)methyl-4-t-butyldimethylsilyloxy)methyl}-1H-imidazol-5-yl]-2-benzyl-2-propenoate, prepared as in Example 28, followed by manganese dioxide oxidation of the 4-hydroxymethyl group to the carboxaldehyde; mp 187°–188° C.

EXAMPLE 41

3-1-(2-(1-Adamantyl)ethyl-2-n-butyl-1H-imidazol-5-yl]-2-(4-methoxy-phenyl)methyl-2-propenoic Acid A mixture of 2-(1-adamantyl)ethanol (10.7 g) and diisopropylethylamine (11 ml) in methylene chloride (70 ml) was added to triflic anhydride (16.75 g) in 70 ml of methylene chloride at −78° C. under argon. After stirring the mixture at −78° C. for 45 minutes, 1-acetyl-2-n-butyl- 5-(acetoxymethyl)imidazole in 50 ml of methylene chloride was added and the mixture was allowed to stand at room temperature for 4 days, then concentrated and heated on a steam bath with 10% sodium hydroxide (250 ml), diluted with 300 ml of water extracted with methylene chloride, dried, filtered and concentrated to give an oil. Chromatography (silica gel) in methanol-chloroform gave 5-acetoxy-methyl-1.-[2-(1-adamantyl)ethyl]-2-n-butylimidazole.

The above prepared compound (5.4 g) was stirred at room temperature with potassium hydroxide (5.2 g) in ethanol (200 ml) for one hour. The mixture was concentrated, poured into water, stirred and filtered to give 1-[2-(1-adamantyl)ethyl]-2-n-butyl-5-hydroxymethylimidazole.

The hydroxymethyl group is oxidized by refluxing the imidazole compound with manganese dioxide in toluene to give 1-[2-(1-adamantyl)ethyl]-2-n-butylimidazol-5-carboxaldehyde.

Diisopropylamine (0.563 g) is covered with 5 ml of tetrahydrofuran and 2 ml of 2.5 M n-butyl lithium in hexane is added. The mixture is stirred for 15 minutes and methyl 3-(4-methoxyphenyl)propanoate (0.97 g) is added in 3 ml of tetrahydrofuran. After 20 minutes, 1.04 g of 1-[2-(1-adamantyl)ethyl]-2-n-butylimidazol-5-carboxaldehyde in 3 ml of tetrahydrofuran is added and the mixture is stirred for 30 minutes at −78° C. The mixture is poured into 40 ml of saturated ammonium chloride in water, extracted with ether, dried, filtered, concentrated and chromatographed on silica gel eluting with 70% ethyl acetate-30% hexane to give methyl 3-[1-(2-(1-adamantyl)ethyl)-2-n-butyl-1H-imidazol-5-yl)-3-hydroxy-2-(4-methoxyphenyl)methyl propanoate. This compound is reacted with acetic anhydride in methylene chloride with 4-dimethylaminopyridine at room temperature to give the corresponding 3-acetoxy compound. The above prepared 3-acetoxy compound in toluene is heated with 1,8-diazobicyco[5,4,0]undec-7-ene by the process of Example 29(iii) to give methyl 3-[1-(2-(1-adamantyl)ethyl)-2-n-butyl-1H-imidazol-5-yl]-2-(4-methoxyphenyl)methyl-2-propenoate.

The ester is hydrolyzed in ethanol using potassium hydroxide to give the title compound.

EXAMPLE 42

(E)-3-[2-n-Butyl-1-{(2-chlorophenyl)methyl}-4-carboxy-1H-imidazol-5-yl]-2benzyl-2-propenoic Acid (E)-3-[2-n-Butyl-1-[(2-chlorophenyl)methyl]-4-hydroxymethyl-1H-imidazol-5-yl]-2-benzyl-2-propenoic acid, prepared as in Example 28, is esterified with p-methoxy-benzyl alcohol to give the p-methoxy-benzyl propenoate. The 4-hydroxymethyl group is oxidized using Jones reagent in acetone and the ester is hydrolized using 10% sodium hydroxide to give the title compound.

EXAMPLE 43

(E)-3-[2-n-Butyl-1-{(2-chlorophenyl)methyl}-4-carbamoyl-1H-imidazol-5-yl]-2-benzyl-2-propenoic Acid p-Methoxybenzyl (E)-3-[2-n-butyl-1-[(2-chlorophenyl)methyl]-4-carboxy-1H-imidazol-5-yl]-2-benzyl-2-propenoate, prepared as in Example 42, is treated with oxalyl chloride in methylene chloride at 0° C. to give the 4-chloroformyl imidazole which is treated with ammonium hydroxide and the ester is hydrolized to give the title compound.

EXAMPLE 44

(E)-3-2-n-Butyl-1-{(4-carboxy-2-chlorophenyl)methyl}-1H-imidazol-5-yl-2-benzyl-2-propenoic Acid A suspension of 2-butylimidazol-5-aldehyde (16.92 g, 0.111 mmol, prepared by manganese dioxide oxidation of the alcohol, prepared in Example 1), chloromethyl pivalate (21.77 g, 0.145 mmol), and potassium carbonate (20.07 g, 0.145 mmol) in 200 ml of dimethylformamide was stirred at ambient temperature under argon for four days The solids were removed by filtration and washed with ether. The combined filtrates were partitioned between ether and water. The ether phase was washed successively with water and brine, dried over magnesium sulfate and concentrated under vacuum to give 23.6 g of 2-n-butyl-1-pivalyloxy-methylimidazole-5-aldehyde A mixture of ethyl 4-bromomethyl-3-chlorobenzoate (5.28 g, 0.020 mmol, U.S. Pat. No. 4,837,333) and 2-n-butyl-1-pivalyloxymethyl-imidazole-5-aldehyde (4.45 g, 0.0167 mol) was heated at 100° C. under argon for 18 hours. Repeated trituration with ether gave 6.38 g of a crystalline salt. A suspension of this salt in 100 ml of ethyl acetate Was stirred for 0.5 hours with 100 ml of 5% aqueous sodium carbonate. The layers were separated, the aqueous layer washed with ethyl acetate, and the combined organic layers washed with water, dried over magnesium sulfate and concentrated to give an oil. Chromatography of this oil over silica gel eluting with ethyl acetate/hexane (1:1) gave 1.02 g of 2-n-butyl-1-[(4-carboethoxy-2-chlorophenyl)methyl]imidazole-5-aldehyde.

Ethyl 2-carboxy-3-phenylpropionate is prepared by stirring a solution of diethyl 2-benzylmalonate and potassium hydroxide in ethanol under argon at room temperature for 12 days and then purifying by removing the solvent under vacuum, dissolving the reside in water, washing the aqueous layer with aqueous hydrochloric acid and with ether.

A solution of this half-acid half-ester in toluene is added to a refluxing solution of 2-n-butyl-1-(4-carboethoxy-2-chlorobenzyl)imidazole-5-aldehyde and piperidine in toluene. Twice at 1 hour intervals an additional amounts of the half-acid, half-ester is added, and the solution is then refluxed for 17 hours. Evaporation of the toluene and chromatography of the residue over silica gel using 2:3 ethyl acetate-hexane for elution gives the diester of the title product. This diester is hydrolyzed in 2:1 ethanol-water with 5 equivalents of potassium hydroxide for 18 hours and worked up in the usual manner to give the final product.

EXAMPLE 45

(E)-3-[2-n-Butyl-1-{(4-carboxyphenyl)methyl}-H-imidazole-5-yl]-2-benzyl-2-propenoic Acid The title compound was prepared following the procedure of Example 44 replacing ethyl 4-bromomethyl-3-chlorobenzoate with methyl 4-bromomethylbenzoate; mp 265°–267° C.(d).

EXAMPLE 46

(E)-3-[2-n-Butyl-1-{(4-sulfonamidophenyl)-methyl}-1H-imidazol-5-yl]-2-benzyl-2-propenoic Acid The procedure of Example 44 is followed using 4-bromomethylbenzenesulfonamide (Braselton, et al., Anal. Chem., 48, 1386 (1976)) in place of methyl 4-bromomethyl-3-chlorobenzoate to give the title compound.

EXAMPLE 47

(E)-3-[2-n-Butyl-1-{(4-carboxy-2-nitrophenyl)-methyl)}-1H-imidazol-5-yl]-2-benzyl-2-propenoic Acid The procedure of Example 44 is followed using methyl 4-bromomethyl-3-nitrobenzoate (prepared from 4-methyl-3-nitrobenzoic acid by esterification with gaseous hydrochloric acid-methanol followed by methyl bromination with N-bromosuccinimide) to give the title compound.

EXAMPLE 48

(E)-3-2-n-Butyl-1-{(4carboxy-3-chlorophenyl)methyl}-1H-imidazol-5-yl]-2-benzyl-2-propenoic Acid The procedure of Example 44 is followed using ethyl 4-bromomethyl-2-chlorobenzoate (U.S. Pat. No. 4,837,333) in place of ethyl 4-bromomethyl-3-chlorobenzoate to give the title compound.

EXAMPLE 49

(E)-3-1-{(2-Chlorophenyl)methyl}-2-propylthio-1H-imidazol-5-yl]-2-benzyl-2-propenoic Acid (i)

5-carboxymethyl-1-(2-chlorophenyl)methyl-2-thio-1H-imidazole

A solution of 2-chlorobenzylamine (14.2 g, 0.1 mol) and triethylamine (13.9 ml, 0.1 mol), in dimethylformamide (100 ml) was treated with methyl chloroacetate (10.9 g, 0.1 mol), and the mixture was heated at 50° C. for 3.5 hours. The cooled reaction mixture was diluted with ether, the solids filtered and the concentrated filtrate was flash chromatographed over silica gel with 6:5 hexane in ethyl acetate to provide 15.3 g (71%) of homogeneous methyl 2-[N-(2-chlorophenyl)methyl]-aminoacetate. This product (15.2 g, 0.071 mol) in mixed xylenes (100 ml) was treated with 98% formic acid (2.74 ml, 0.0711 mol) and the mixture was refluxed from 2.5 hours with a Dean-Stark water separator. Evaporation gave 17.1 g (99%) of methyl 2-[N-(2-chlorophenyl)-methyl-N-formyl)aminoacetate. This formylated product (17.0 g, 0.071 mol) was dissolved in methyl formate (13.3 ml, 0.216 mol) and added dropwise to a sodium methoxide mixture prepared by adding sodium metal (1.79 g, 0.0778 g-atom) to tetrahydrofuran (325 ml) followed by slow addition of methanol (3.15 ml, 0.0778 mol). The combined mixture was stirred at room temperature for 18 hours, then evaporated to dryness This crude product was dissolved in 50% aqueous methanol (200 ml), treated with charcoal, filtered and the solution was cooled in ice. Concentrated hydrochloric acid followed by a solution of potassium thiocyanate (8.6 g, 0.0885 mol) in water (20 ml). The mixture was heated in an oil bath held at 90° C. for 2.5 hours, then cooled to −10° C. The precipitated solid was filtered, washed with cold ethanol-water and dried at 60° C. to provide 14.7 g (74%) of 5-carboxymethyl-1-(2-chlorophenyl)-methyl-2-thio-1H-imidazole; mp 72°-74° C.

(ii)

1-(2-chlorophenyl)methyl-5-carboxymethyl-2-propylthio-1H-imidazole

A mixture of 5-carboxymethyl-1=(2-chlorophenyl)-methyl-2-thio-1H-imidazole (2 g, 7.08 mmol, ethyl acetate (20 ml), 5% sodium carbonate solution (40 ml) and propyl bromide (4 ml, 44 mmol) was heated at 60° C. for 18 hours. The organic layer was separated, dried over magnesium sulfate and concentrated to 2.23 g of crude product. Trituration with ether provided 1.63 g (71%) of 5-carboxymethyl-1-(2-chlorophenyl)methyl-2-propylthio-1H-imidazole; mp 68°-71° C. (from hexane).

(iii)

(E)-3-[1-(2-chlorophenyl)methyl-2-propylthio-1H-imidazol-5-yl]-2-benzyl-2-propenoic acid A solution of 5-carboxymethyl-1-(2-chlorophenyl)-methyl-2-propylthio-1H-imidazole (3.74 g, 11.5 mmol) in dry tetrahydrofuran (50 ml) was cooled to −78° C. under argon, and a solution of diisobutyl alumninum hydride in toluene (30 ml of 1M) was added dropwise. The mixture was stirred at −78° C. for 1.5 hours, then allowed to slowly warm to room temperature. The reaction was quenched by pouring onto iced dilute acetic acid, the product was extracted into methylene chloride and the organic extracts were washed with water, 5% sodium carbonate solution and brine The dried, concentrated product was a light tan solid (3.32 g). Crystallization from ethanol/water gave 1-(2-chlorophenyl)methyl-5-hydroxymethyl-2-propylthio-1H-imidazole; mp 98°-101° C.

The title compound is prepared by the procedure of hydroxymethyl-2-propylthio-1H-imidazole in place of 2-n-butyl-1-(2-chlorophenyl)methyl-5-hydroxymethyl-1H-imidazole.

EXAMPLE 50

(E)-3-[{1-(2-Corophenyl)methyl}-2-propenylthio-1H-imidazol-5-yl]-2-benzyl-2-propenoic Acid The title compound is prepared following the procedure of Example 49 using allyl bromide in place of propyl bromide.

EXAMPLE 51

(E)-3-[{1-(2-Chorophenyl)methyl}-2-pentylthio-1H-imidazol-5-y11-2-benzyl2-propenoic Acid The title compound is prepared following the procedure of Example 49 using 1-bromopentane in place of propyl bromide.

EXAMPLE 52

(E)-3-[{1-(2-Chorophenyl)methyl}-2-benzylthio-1H-imidazol-5-yl]-2-benzyl-2-propenoic Acid The title compound is prepared following the procedure of Example 49 using benzyl bromide in place of propyl bromide.

EXAMPLE 53

(E)-3-[{1-(2-Chorophenyl)methyl}-2-cyclohexylthio-1H-imidazol-5-yl]-2-benzyl-2-propenoic Acid The title compound is prepared following the procedure of Example 49 using cyclohexyl bromide in place of propyl bromide.

EXAMPLE 54

(E)-3-[{1-(2-Chorophenyl)methyl}-2-heptylthio-1H-imidazol-5-yl]-2-benzyl-2propenoic Acid The title compound is prepared following the procedure of Example 49 using 1-bromoheptane in place of propyl bromide.

EXAMPLE 55

(E)-3-[{1-(2-Chorophenyl)methyl}-2-hexenylthio-1H-imidazol-5-yl]-2-benzyl-2-propenoic Acid The title compound is prepared following the procedure of Example 49 using 6-bromo-1-hexene in place of propyl bromide.

EXAMPLE 56

(E)-3-[{1-(2-Chorophenyl)methyl}-cyclopropylthio-1H-imidazol-5-yl]-2-benzyl-2-propenoic Acid The title compound is prepared following the procedure of Example 49 using cyclopropyl bromide in place of propyl bromide.

EXAMPLE 57

(E)-3-[2-n-Butyl-1-{[2-chloro-4(1H-tetrazol-5-yl)phenyl]methyl}-1H-imidazol-5-yl]-2-benzyl-2-propenoic Acid The procedure of Example 42 is followed using t-butyl 4-bromomethyl-3-chlorobenzoate (prepared from 3-chloro-4-methylbenzoic acid by esterification with 2-methylpropene in the presence of concentrated sulfuric acid, followed by bromination with N-bromosuccinimide) in place of ethyl 4-bromomethyl-3-chlorobenzoate to give ethyl (E)-3-[2-n-butyl-1-{[2-chloro-4-(carbo-t-butoxy)phenyl]-methyl}-1H-imidazol-5-yl]-2-benzyl-2-propenoate. The t-butyl ester is removed with trifluoroacetic acid.

To a suspension of ethyl (E)-3-[2-n-butyl-1-{(2-chloro-4-carboxyphenyl)methyl}-1H-imidazol-5-yl]-2-benzyl-2-propenoate in benzene is added thionyl chloride. The resultant mixture is heated to 50° C. for 90 minutes, then evaporated to an oily residue. The residue is taken up in hexane and evaporated again. The acid chloride is treated with concentrated ammonium hydroxide and then the reaction mixture is stirred for 16 hours at room temperature. The solid is filtered, washed with water, and dried at 50° C. under vacuum to yield the primary amide derivative.

To a solution of dimethylformamide in acetonitrile is added oxalyl chloride at 0° C. under argon. After 3 minutes, a solution of the amide prepared above in dimethylformamide is added via a cannula. Five minutes later, pyridine is added; the reaction mixture is stirred for an additional 5 minutes at 0° C., then partitioned between ethyl acetate and 50% aqueous ammonium chloride The ethyl acetate layer is washed with water and brine. The ethyl acetate extract is dried with anhydrous sodium sulfate and evaporated to give the corresponding nitrile derivative.

Tetrahydrofuran is added under argon with stirring to a mixture of the nitrile prepared above and aluminum chloride. Sodium azide is added all at once, followed by a tetrahydrofuran rinse, and the reaction is heated to 65° C. for 22 hours, then cooled to room temperature. The reaction mixture is diluted with ethyl acetate and treated with 10% hydrochloric acid solution with vigorous stirring for 5 minutes. The ethyl acetate layer is washed with water and brine. The ethyl acetate layer is dried with anhydrous sodium sulfate and evaporated to give ethyl (E)-3-[2-n-butyl-1-{[2-chloro-4-(1H-tetrazol-5-yl)phenyl]methyl}-1H-imidazol-5-yl]-2-benzyl-2-propenoate.

The title propenoic acid compound is prepared from the above ethyl ester by basic hydrolysis using aqueous base in methanol.

EXAMPLE 58

(E)-2-n-Butyl-1-{(2-nitrophenyl)methyl}-1H-imidazol-5-yl]-2-benzyl-2-propenoic Acid The title compound is prepared following the procedure of Example 1 using 2-nitrobenzyl bromide in place of 2-chlorobenzyl bromide.

EXAMPLE 59

(E)-[2-n-Butyl-1-{(3-nitrophenyl)methyl}-1H-imidazol-5-yl]-2-benzyl-2-propenoic Acid The title compound is prepared following the procedure of Example 1 using 3-nitrobenzyl bromide in place of 2-chlorobenzyl bromide.

EXAMPLE 60

(E)-2-n-Butyl-1-{(4-nitrophenyl)methyl}-1H-imidazol-5-yl]-2-(2-benzyl)-2propenoic Acid The title compound is prepared following the procedure of Example 1 using 4-nitrobenzyl bromide in place of 2-chlorobenzyl bromide.

EXAMPLE 61

(E)-[2-n-Butyl-1-{(2-trifluoromethylphenyl)methyl}-1H-imidazol-5-yl]-2-benzyl-2-propenoic Acid The title compound is prepared following the procedure of Example 1 using 2-trifluoromethylbenzyl bromide in place of 2-chlorobenzyl bromide.

EXAMPLE 62

(E)-[2-n-Butyl-1-{(2,3-dichlorophenyl)methyl}-1H-imidazol-5-yl]-2-benzyl-2-propenoic Acid The title compound is prepared following the procedure of Example 1 using 2,3-dichlorobenzyl bromide in place of 2-chlorobenzyl bromide.

EXAMPLE 63

(E)-[2-n-Butyl-1-{(3-methoxy-2-nitrophenyl)methyl}-1H-imidazol-5-yl]-2-benzyl-2-propenoic Acid The title compound is prepared following the procedure of Example 1 using 3-methoxy-2-nitrobenzyl bromide in place of 2-chlorobenzyl bromide.

EXAMPLE 64

(E)-[2-n-Butyl-1-{(2-cyanophenyl)methyl}-1H-imidazol-5-yl]-2-benzyl-2-propenoic Acid The title compound is prepared following the procedure of Example 1 using 2-cyanobenzyl bromide in place of 2-chlorobenzyl bromide.

EXAMPLE 65

(E)-[2-n-Butyl-1-{(4-methoxy-3-methyl)methyl}-1H-imidazol-5-yl]-2-benzyl-2-propenoic Acid The title compound is prepared following the procedure of Example 1 using 4-methoxy-3-methylbenzyl bromide in place of 2-chlorobenzyl bromide.

EXAMPLE 66

(E)-[2-n-Butyl-1-{(3-methoxyphenyl)methyl}-1H-imidazol-5-yl]-2-benzyl-2-propenoic Acid The title compound is prepared following the procedure of Example 1 using 3-methoxybenzyl bromide in place of 2-chlorobenzyl bromide.

EXAMPLE 67

(E)-[2-n-Butyl-1-{(2-methoxyphenyl))methyl}-1H-imidazol-5-yl]-2-benzyl-2-propenoic Acid The title compound is prepared following the procedure of Example 1 using 2-methoxybenzyl bromide in place of 2-chlorobenzyl bromide.

EXAMPLE 68

(E)-[2-n-Butyl-1-{(2-hydroxyphenyl)methyl}-1H-imidazol-5-yl]-2-benzyl-2-propenoic Acid The title compound is prepared from the 2-methoxy compound prepared in Example 67 using boron tribromide in methylene chloride.

EXAMPLE 69

(E)-3-[2-n-Hexyl-1-{(4-carboxyphenyl)methyl}-1H-imidazol-5-yl]-2-benzyl-2-propenoic Acid The title compound is prepared following the procedure of Example 1, using n-hexyl iodide in place of n-butyl iodide and using 4-carbomethoxybenzyl alcohol in place of 2-chlorobenzyl alcohol.

EXAMPLE 70

(E)-3-[2-n-Propyl-1-{(2-nitrophenyl)methyl}-1H-imidazol-5-yl]-2-benzyl-2-propenoic Acid The title compound is prepared following the procedure of Example 1 using n-propyl iodide in place of n-butyl iodide and 2-nitrobenzyl alcohol in place of 2-chlorobenzyl alcohol.

EXAMPLE 71

(E)-3-2-n-Butyl-1-{(4-phenyl)methyl}-1H-imidazol-5yl]-2-benzyl-2-propenoic Acid

The title compound was prepared following the procedure of Example 1 replacing 2-chlorobenzyl bromide with 4-phenylbenzyl bromide; mp 198°-200° C.

EXAMPLE 72

(E)-3-[2-n-Butyl-1-{(2-phenylphenyl)methyl}-1H-imidazol-5-yl]-2-benzyl-2-propenoic Acid The title compound was prepared following the procedure of Example 1 replacing 2-chlorobenzyl bromide with 2-phenylbenzyl bromide; mp 221°-224° C.

EXAMPLE 73

(E)-3-2-n-Butyl-1-{(2-chlorophenyl)methyl}-1H-imidazol-5-yl]-2-(3-methoxyphenyl)methyl-2-propenoic Acid The title compound was prepared following the procedure of Example 27 replacing methyl 3-(3,4-methylene-dioxyphenyl)propanoate with methyl-3-(3-methoxyphenyl)-propanoate; mp 173°-174° C.

EXAMPLE 74

(E)-3-[2-n-Butyl-1-{(2-chlorophenyl)methyl}-1H-imidazol-5-yl]-2-(3,4-dihydroxyphenyl)methyl-2-propenoic Acid (E)-3-[2-n-Butyl-1-{(2-chlorophenyl)methyl}-1H-imidazol-5-yl]-2-(3,4-dimethoxyphenyl)methyl-2-propenoic acid, prepared in Example 28, was treated with boron tribromide in methylene chloride to give the title compound; mp 129-133° C.

EXAMPLE 75

(E)-3-[2-n-Butyl-1-{(2-chlorophenyl)methyl}-1H-imidazol-5-yl]-2-(4-nitrophenyl)methyl-2-propenoic Acid The title compound was prepared following the procedure of Example 27 replacing methyl (3,4-methylenedioxyphenyl)propanoate with methyl (4-nitrophenyl)propanoate; mp 207°-208° C.

EXAMPLE 76

(E)-3-[2-n-Butyl-1-{(2-chlorophenyl)methyl}-1H-imidazol-5-yl]-2-(4-dimethylaminophenyl)methyl-2-propenoic Acid The title compound was prepared following the procedure of Example 27 replacing methyl (3,4-methylenedioxyphenyl)propanoate with methyl(4-dimethylaminophenyl)-propanoate; mp 171°-172° C.

EXAMPLE 77

(E)-3-[2-n-Butyl-1-{(2-chlorophenyl)methyl}-1H-imidazol-5-yl]-2-(4-aminophenyl)methyl-2-propenoic Acid The title compound was prepared following the procedure of Example 27 replacing methyl (3,4-methylenedioxyphenyl)propanoate with methyl (4-aminophenyl)propanoate; mp 191°-192° C.

EXAMPLE 78

(E)-3-[1-{(2-Chlorophenyl)methyl}-2-phenyl-1H-imidazol-5-yl]-2-benzyl-2-propenoic Acid The title compound was prepared following the procedure of Example 1, replacing n-butyl iodide with phenyl bromide; mp 211°-213° C.

EXAMPLE 79

(E)-3-[2-n-Butyl-1-{(2-chlorophenyl)methyl}-1H-imidazol-5-yl]-2-[1-phenyl-1-phenylmethyl]-2-propenoic Acid The title compound is prepared using the procedure of Example 27, replacing methyl 3-(3,4-methylenedioxyphenyl)propanoate with methyl 3-phenyl-3-phenylpropanoate [prepared following the procedure described in Tetra, 44 (7) 2055 (1988)].

EXAMPLE 80

(E)-3-[2-n-Butyl-1-{(2-chlorophenyl)methyl}-1H-imidazol-5-yl-2-[2-phenyl-2-phenylethyl]-2-propenoic Acid The title compound is prepared using the procedure of Example 27, replacing methyl 3-(3,4-methylenedioxyphenyl)propionate with methyl 3-phenyl-4-phenylpropanoate [following the procedure described in Tetra, 44 (7) 2055 (1988)].

EXAMPLE 81

(E)-3-[2-n-Butyl-1-{(2-chlorophenyl)methyl}-1H-imidazol-5-yl]-2-{-1-phenylpentyl}-2-propenoic Acid The title compound is prepared using the procedure of Example 27 replacing 3-(3,4-methylenedioxyphenyl)-propionate with methyl 3-phenylheptanoate.

EXAMPLE 82

(E)-3-[2-n-Butyl-1-{2-carboxyphenyl)methyl}-1H-imidazol-5-yl]-2-benzyl-2-propenoic Acid The title compound is prepared using the procedure of Example 44 replacing ethyl 4-bromomethyl-3-chlorobenzoate with ethyl 2-bromomethylbenzoate.

EXAMPLE 83

(E)-3-[2-n-Butyl-1-{(3-carboxyphenyl)methyl}-1H-imidazol-5-yl]-2-benzyl-2-propenoic Acid The title compound is prepared by the procedure of Example 27 using 2-n-butyl-1-[4-carbomethoxyphenyl)-methyl]-imidazole-5-aldehyde, prepared by the method described for the preparation of 2-n-butyl-1-[(4-carboethoxy-2-chlorophenyl)methyl]imidazole-5-aldehyde in Example 44, and methyl 3-phenylpropanoate.

EXAMPLE 84

(E)-3-[2-n-Butyl-1-{(4-hydroxy-3-methylphenyl)methyl}-1H-imidazol-5-yl]-2-benzyl-2-propenoic Acid The title compound is prepared by demethylation of (E)-2-n-butyl-1-{(4-methoxy-3-methylphenyl)methyl}-1H-imidazol-5-yl]-2-benzyl-2-propenoic acid, prepared in Example 36, using boron tribromide in methylene chloride at room temperature.

EXAMPLE 85

(E)-3-[2-n-Butyl-1-{(4-carbomethoxyphenyl)methyl}-1H-imidazol-5-yl]-2-benzyl-2-propenoic Acid The title compound was prepared using 2-n-butyl-1-[(4-carbomethoxyphenyl)methyl]imidazole-5-aldehyde, prepared by the method described for the preparation of 2-n-butyl-1-[(4-carboethoxy-2-chlorophenyl)methyl]imidazole-5-aldehyde in Example 44, and t-butyl 3-phenylpropanoate by the procedure of Example 27, except, instead of basic hydrolysis, trifluoroacetic acid hydrolysis of the t-butyl ester is employed.

EXAMPLE 86

(E)-3-[2-n-Butyl-1-{(4-cyanophenyl)methyl}-1H-imidazol-5-yl]-2-benzyl-2-propenoic Acid The title compound is prepared by the procedure of Example 27, using 2-n-butyl-[(4-cyanophenyl)methyl]imidazole-5-aldehyde, prepared by the method of Example 42 describing the preparation of 2-n-butyl-1-[(4-carboethoxy-2-chlorophenyl)methyl]imidazole-5-aldehyde, and methyl 3-phenylpropanoate, except, instead of basic hydrolysis of the ester with sodium hydroxide, potassium carbonate hydrolysis was employed.

EXAMPLE 87

(E)-3-[2-n-Butyl-1-{(4-carbamoylphenyl)methyl}-1H-imidazol-5-yl]-2-benzyl-2-propenoic Acid Methyl (E)-3-[2-n-butyl-1-{(4-cyanophenyl)methyl}-1H-imidazol-5-yl]-2-benzyl-2-propanoate, prepared in Example 86, is subjected to hydrolysis with concentrated hydrochloric acid to give the title compound.

EXAMPLE 88

(E)-3-[2-n-Butyl-1-{[4-(1H-tetraol-5-yl)phenyl]methyl}-1H-imidazol-5-yl]-2-benzyl-2-propenoic Acid The title compound is prepared from methyl (E)-3-[2-n-butyl-1-{(4-cyanophenyl)methyl}-1H-imidazol-5-yl]-2-benzyl-2-propanoate, prepared in Example 86, using the procedure described in Example 57.

EXAMPLE 89

(E)-3-[2-n-Propyl-1-{(4-carboxyphenyl)methyl}-1H-imidazol-5-yl]-2-benzyl-2-propenoic Acid The title compound is prepared using the procedure of Example 1 replacing valeramidine methyl ether hydrochloride with butyramidine methyl ether hydrochloride and replacing 2-chlorbenzyl alcohol with 4-carbomethoxybenzyl alcohol.

EXAMPLE 90

(E)-3-[2-n-Propyl-1-{(2-chlorophenyl)methyl}-1H-imidazol-5-yl]-2-benzyl-2-propenoic Acid The title compound is prepared using the procedure of Example 1 replacing valeramidine methyl ether hydrochloride with butyramidine methyl ether hydrochloride.

EXAMPLE 91

(E)-3-2-n-Hexyl-1-{(2-chlorophenyl)methyl}-1H-imidazol-5-yl-2-benzyl-2-propenoic Acid The title compound is prepared using the procedure of Example 1 replacing valeramidine methyl ether hydrochloride with caproylamidine methyl ether hydrochloride.

EXAMPLE 92

(E)-3-[2-n-Butyl-1-}(4-carboxy-2,3-dichlorophenyl)methyl}-1H-imidazol-5-yl]-2-benzyl-2-propenoic Acid The title compound is prepared using the procedure of Example 44 replacing ethyl 4-bromomethyl-3-chlorobenzoate with methyl 4-bromomethyl-2,3-dichlorobenzoate (prepared by oxidation of 2,3-dichloro-p-xylene with nitric acid, followed by esterification with methanol/hydrochloric acid and methyl bromoination with N-bromosuccinimide).

EXAMPLE 93

(E)-3-[2-n-Butyl-1-{(4-carboxy-2,5-dichlorophenyl)methyl}-1H-imidazol-5-yl]-2-benzyl-2-propenoic Acid The title compound is prepared using the procedure of Example 44 replacing ethyl 4-bromomethyl-3-chlorobenzoate with methyl 4-bromomethyl-3,6-dichlorobenzoate (prepared by oxidation of 2,5-dichloro-p-xylene with nitric acid, followed by esterification with methanol/hydrochloric acid and methyl bromination with N-bromosuccinimide).

EXAMPLE 94

(E)-3-[2-n-Butyl-1-{(3-carboxynaphthyl)methyl}-1H-imidazol-5-yl]-2-benzyl-2-propenoic Acid The title compound is prepared using the procedure of Example 44 replacing ethyl 4-bromomethyl-3-chlorobenzoate with 4-bromomethylcarbomethoxynaphthalene prepared by the oxidation of 1,4-dimethylnaphthalene with nitric acid, followed by esterification with methanol/hydrochloric acid and methyl bromination with N-bromosuccinimide).

EXAMPLE 95

(E)-3-[2-n-Buyl-1-{(3-carboxynaphthyl)methyl}-1H-imidazol-5-yl]-2-benzyl-2-propenamide (E)-3-[2-n-Butyl-{(2,3-dichlorophenyl)methyl-1H-imidazol- 5-yl]-2-benzyl-2-propenoic acid, prepared in Example 62, is treated with thionyl chloride and then ammonium hydroxide, as described in Example 57, to give the title compound.

EXAMPLE 96

(E)-3-[2-n-Butyl-1-{(4-carbamoylphenyl)methyl}-1H-imidazol-5-yl]-2-(2-benzyl)-2-propenamide (E)-3-[2-n-Butyl-1-{(t-carboxyphenyl)methyl}-1H-imidazol-5-yl]-2-benzyl-2-propenoic acid, prepared in Example 44, is treated with trifluoroacetic acid, thionyl chloride, and then ammonium hydroxide, as described in Example 57, to give the title compound.

EXAMPLE 97

(E)-3-[2-n-Butyl-1-{(2-nitrophenyl)methyl}-1H-imidazol-5-yl]-2-benzyl-2-propenamide (E)-3-[2-n-Butyl-1-{(2-nitrophenyl)methyl}-1H-imidazol-5yl]-2-benzyl-2-propenoic acid, prepared in Example 58, is treated with thionyl chloride and then ammonium hydroxide, as described in Example 57, to give the title compound.

EXAMPLE 98

E-3-[2-n-Butyl-1-{(2-chlorophenyl)methyl}-1H-imidazol-5-yl]-2-benzyl-2-propenoxy Acetic Acid To a suspension of sodium hydride (2.3 mml)in 5 mL of glyme is added portionwise (E)-3-[2-n-butyl-1-{(2-chlorophenyl)methyl}-1H-imidazol-5-yl]-2-benzyl-2-propenol prepared by the method of Example 18(i) from the methyl ester of the compound of Example 2. After stirring for 30 minutes, methyl bromoacetate (2.2 mmol) is added dropwise The reaction is stirred overnight at room temperature and then the mixture is poured into ice/water. The product is extracted into ethyl acetate (3×). The combined organic extracts are washed with water and brine and dried with anhydrous magnesium sulfate. The solvent is removed in vacuo. The residue is chromatographed on silica gel to give the esters of the title compound as an oil.

The ester is saponified by base as described in Example 1.

EXAMPLE 99

(E)-3-[2-n-Butyl-1-{(2-chlorophenyl)methyl}-1H-imidazol-5-yl]-2-benzyl-2-propenoic Acid To a solution of (E)-3-[2-n-butyl-1-{(2-chlorophenyl)methyl-1H-imidazol-5-yl]-2-benzyl-2-propenoic acid (1.2 mmol), prepared in Example 1, in tetrahydrofuran (12 mL) is added N-hydroxysuccinimide (1.33 mmol), followed by dicyclohexylcarbodiimide (1.2 mmol) in 5 mL of tetrahydrofuran. The reaction mixture is heated at 35° C. for one hour and then glycine methyl ester hydrochloride (1.57 mmol) and triethylamine (1.57 mmol) are added. The reaction is stirred at room temperature overnight. The mixture is diluted with 20 mL of ethyl acetate and the solids are filtered. The filtrate is concentrated to dryness and the residue is chromatographed on silica gel to give the ester-amide as an oil.

The ester is saponified to the title acid compound by base hydrolysis, as described in Example 1.

EXAMPLE 100

(E)-3-[2-n-Butyl-1-{(2-chlorophenyl)methyl}-1H-imidazol-5-yl]-2-benzyl-2-propenamide (E)-3-[2-n-Butyl-1-{(2-chlorophenyl)methyl}-1H-imidazol-5-yl]-2-benzyl-2-propenoic acid, prepared in Example 2, is treated with thionyl chloride and then ammonium hydroxide, as described in Example 57, to give the title compound.

EXAMPLE 101

(E)-2-[2-n-Butyl-1-{(2-chlorophenyl)methyl}-1H-imidazol-5-yl]-2-benzyl-2-propenamide (E)-3-[2-n-Butyl-1-{(2-chlorophenyl)methyl}-1H-imidazol-5-yl]-2-benzyl-2-propenoic acid, prepared in Example 61, is treated with thionyl chloride and then ammonium hydroxide, as described in Example 57, to give the title compound.

EXAMPLE 102

Ethyl (E)-3-[2-n-butyl-1-{(4-carbomethoxyphenyl)methyl}-1H-imidazol-5-yl]-2-benzyl-2-propanoate The title compound is prepared following the procedure of Example 27 using 2-n-butyl-1-[(4-carbomethoxyphenyl)-methyl]imidazole-5-aldehyde, prepared by the method described for the preparation of 2-n-butyl-1-[(4-carboethoxy-2-chlorophenyl)methyl]imidazole-5-aldehyde in Example 44, and ethyl 3-(2-thienyl)-propanoate.

EXAMPLE 103

(E)-3-[2-n-Butyl-1-}(4-carboxyphenyl)methyl}-1H-imidazol-5-yl]-2-n-butyl-2-propenoic Acid The title compound was prepared following the procedure of Example 1; mp 263°–265° C.(d)

EXAMPLE 104

An oral dosage form for administering orally active Formula (I) compounds is produced by screening, mixing nd filling into hard gelatin capsules the ingredients in proportions, for-example, as shown below.

| Ingredients | Amounts |
| --- | --- |
| (E)-3-[2-n-butyl-1-{(4-carboxy)methyl}-1H-imidazol-5-yl]-2-benzyl-methyl-2-propenoic acid | 100 mg |
| magnesium stearate | 10 mg |
| lactose | 100 mg |

EXAMPLE 105

The sucrose calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
| --- | --- |
| (E)-3-[2-n-butyl-1-{(2-chlorophenyl)-methyl}-1H-imidazol-5-yl]-2-(4- | 75 mg |

-continued

| Ingredients | Amounts |
|---|---|
| methoxyphenyl)methyl-2-propenoic acid calcium sulfate dihydrate | 100 mg |
| sucrose | 15 mg |
| starch | 8 mg |
| talc | 4 mg |
| stearic acid | 2 mg |

EXAMPLE 106

(E)-3-[2-n-Butyl-1-{(4-carboxyphenyl)methyl}-1H-imidazol-5-yl]-2-(benzyl-2-propenoic acid, 50 mg, is dispersed in 25 ml of normal saline to prepare an injectable preparation.

EXAMPLE 107

A topical ophthamological solution for administering Formula (I) compounds is produced by mixing under sterile conditions the ingredients in proportions, for example, as shown below.

| Ingredients | Amounts (mg/ml) |
|---|---|
| (E)-3-[2-n-butyl-1-[(2-chlorophenyl)-methyl]-1H-imidazol-5-yl]-2-(3,4-dimethoxyphenyl)methyl-2-propenoic acid | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 mL |
| 1.0 N sodium hydroxide | q.s. ad pH 7.4 |

It is to be understood that the invention is not limited to the embodiments illustrated hereabove and the right to the illustrated embodiments and all modifications coming within the scope of the following claims is reserved.

What is claimed is:

1. A compound of the formula.

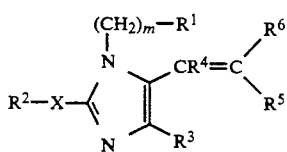

in which:
 R$^1$ is adamantyl, phenyl, biphenyl, or naphthyl, with each aryl group being unsubstituted or substituted by one to three substituents selected, from Cl, Br, F, I, C$_1$-C$_6$alkyl, nitro, CO$_2$R$^7$, tetrazol-5-yl, C$_1$-C$_6$alkoxy, hydroxy, SC$_1$-C$_6$alkyl, SO$_2$NHR$^7$, NHSO$_2$R$^7$, SO$_3$H, CONR$^7$R$^7$, CN, SO$_2$C$_1$-C$_6$alkyl, NHSO$_2$R$^7$, PO(OR$^{7'}$)$_2$, NR$^7$R$^7$, NR$^7$COH, NR$^7$COC$_1$-C$_6$alkyl, NR$^7$CON(R$^7$)$_2$,
 m is 0-4;
 R$^2$ is C$_2$-C$_{10}$alkyl, C$_3$-C$_{10}$alkenyl, C$_3$-C$_{10}$alkynyl, C$_3$-C$_6$cycloalkyl, or (CH$_2$)$_{0-8}$phenyl unsubstituted or substituted by one to three substituents selected from C$_1$-C$_6$alkyl, nitro, Cl, Br, F, I, hydroxy, C$_1$-C$_6$alkoxy, NR$^7$R$^7$, CO$_2$R$^7$, CN, CONR$^7$R$^7$, tetrazol-5-yl, NR$^7$COC$_1$-C$_6$alkyl, SC$_1$-C$_6$alkyl, or SO$_2$C$_1$-C$_6$alkyl;
 X is a single bond, R$^3$ is hydrogen, Cl, Br, F, I, CHO, hydroxymethyl, COOR$^7$, CONR$^7$R$^7$, NO$_2$, CN, NR$^7$R$^7$, or phenyl;
 R$^4$ and R$^5$ are independently hydrogen, C$_1$-C$_6$alkyl, phenyl-Y-, naphthyl-Y-, or biphenyl-Y-, wherein the aryl groups are unsubstituted or substituted by one to three substituents selected from Cl, Br, F, I, C$_1$-C$_6$alkoxy, hydroxy, CO$_2$R$^7$, CN, NO$_2$, tetrazol-5-yl, SO$_3$H, CF$_3$, CONR$^7$R$^7$, SO$_2$NHR$^7$, C$_1$-C$_6$alkyl, or NR$^7$R$^7$, or by methylenedioxy, phenoxy or phenyl, except that R$^4$ and R$^5$ are not both selected from hydrogen;
 Y is a single bond, O, S, or C$_1$-C$_6$alkyl which is straight or branched or optionally substituted by phenyl or benzyl, wherein each of the aryl groups is unsubstituted or substituted by halo, NO$_2$, CF$_3$, C$_1$-C$_4$alkyl, C$_1$-C$_4$alkoxy, CN, or CO$_2$R$^7$;
 R$^6$ is —Z—COOR$^8$ or —Z—CONR$^7$R$^7$;
 Z is a single bond, vinyl, —CH$_2$—O—CH$_2$—, methylene optionally substituted by C$_1$-C$_4$alkyl, one or two benzyl groups, thienylmethyl, or furylmethyl, or —C(O)NHCH-R$^9$—, wherein R$^9$ is H, C$_1$-C$_4$alkyl, phenyl, benzyl, thienyl-methyl, or furylmethyl;
 each R$^7$ independently is hydrogen, C$_1$-C$_4$alkyl, or (CH$_2$)$_m$phenyl, wherein m is 0-4; and
 R$^8$ is hydrogen, C$_1$-C$_6$alkyl, or 2-di(C$_1$-C$_4$alkyl)amino-2-oxoethyl; or
 R$^5$ and R$^6$ are both hydrogen, R$^4$ is —Z—COOR$^8$ wherein R$^8$ is as defined above and Z is other than a single bond; or a pharmaceutically acceptable salt thereof.

2. A compound of claim 1 in which one of R$^4$ and R$^5$ is hydrogen or C$_1$-C$_4$alkyl.

3. A compound of claim 2 in which R$^1$ is phenyl unsubstituted or substituted by one to three substitutents selected from chloro, fluoro, trifluoromethyl, nitro, methyl, methoxy, hydroxy, sulfamyl, cyano, carboxy, carboC$_1$-C$_4$alkoxy, carbamoyl, or tetrazol-5-yl.

4. A compound of claim 3 in which R$^2$ is C$_2$-C$_8$alkyl;

5. A compound of claim 4 in which R$^3$ is hydrogen, chloro, fluoro, or trifluoromethyl and R$^4$ is hydrogen or C$_1$-C$_4$alkyl.

6. A compound of claim 5 in which R$^6$ is COOH and each R$^7$ independently is H or CH$_3$.

7. A compound of claim 6 in which R$^5$ is C$_3$-C$_6$alkyl or benzyl unsubstituted or substituted by one to three substituents selected from Cl, Br, F, NO$_2$, OCH$_3$, OH, CF$_3$, NR$^7$R$^7$, CH$_3$, or CO$_2$R$^7$, or methylenedioxy.

8. A compound of claim 7 which is the E isomer, wherein the R$^6$ group and the imidazole are trans to each other.

9. A compound of claim 8 which is (E)-3-[2-n-butyl-1-{(4-carboxyphenyl)methyl}-1H-imidazol-5-yl]-2-benzyl-2-propenoic acid or a pharmaceutically acceptable salt thereof.

10. A compound of claim 8 which is (E)-3-[2-n-butyl-1-{(2-chlorophenyl)methyl}-1H-imidazol-5-yl]-2-(3,4-dimethoxyphenyl)methyl-2-propenoic acid or a pharmaceutically acceptable salt thereof.

11. A compound of claim 8 which is (E)-3-[2-n-butyl-1-{(2-chlorophenyl)methyl}-1H-imidazol-5-yl]-2-(3,4-methylenedioxyphenyl)methyl-2-propenoic acid or a pharmaceutically acceptable salt thereof.

12. A compound of claim 8 which is (E)-3-[2-n-butyl-1-{(4-carboxyphenyl)methyl}-1H-imidazol-5-yl]-2-n-butyl-2-propenoic acid or a pharmaceutically acceptable salt thereof.

13. A compound of claim 8 which is:

(E)-3-[2-n-butyl-1-{(2-chlorophenyl)methyl}-1H-imidazol-5-yl]-2-(4-methoxyphenyl)methyl-2-propenoic acid;

(E)-3-[2-n-butyl-1-{(2-chlorophenyl)methyl}-1H-imidazol-5-yl]-2-benzyl-2-propenoic acid;

(E)-3-[2-n-butyl-1-{(2-chloro-6-fluorophenyl)methyl}-1H-imidazol-5-yl-2-benzyl-2-propenoic acid;

(E)-3-[2-n-butyl-1-{(2-chlorophenyl)methyl}-4-chloro-1H-imidazol-5-yl]-2-benzyl-2-propenoic acid;

(E)-3-[2-n-butyl-1-{(2-chlorophenyl)methyl}-1H-imidazol-5-yl]-2-(3,4-dihydroxyphenyl)methyl-2-propenoic acid;

(E)-3-[2-n-butyl-1-{(2-chlorophenyl)methyl}-1H-imidazol-5-yl]-2-(2-nitrophenyl)methyl-2-propenoic acid;

(E)-3-[2-n-butyl-1-{(2-chlorophenyl)methyl}-1H-imidazol-5-yl]-2-(4-N,N-dimethylaminophenyl)-methyl-2-propenoic acid; or (E)-3-[2-n-butyl-1-{(2-chlorophenyl)methyl}-1H-imidazol-5-yl]-2-(4-aminophenyl)methyl-2-propenoic acid; or a pharmaceutically acceptable salt thereof.

14. A pharmaceutical composition comprising a pharmaceutical carrier and a compound of claim 1.

15. A pharmaceutical composition of claim 14 in which the compound is (E)-3-[2-n-butyl-1-{(4-carboxyphenyl)methyl}-1H-imidazol-5-yl]-2-benzyl-2-propenoic acid.

16. A pharmaceutical composition of claim 14 in which the compound is (E)-3-[2-n-butyl-1-{(4-carboxyphenyl)methyl}-1H-imidazol-5-yl]-2-n-butyl-2-propenoic acid.

17. A pharmaceutical composition of claim 14 in which the compound is (E)-3-[2-n-butyl-1-{(2-chlorophenyl)methyl}-1H-imidazol-5-yl]-2-(3,4-dimethoxyphenyl)methyl-2-propenoic acid.

18. A pharmaceutical composition of claim 14 in which the compound is (E)-3-[2-n-butyl-1-{(2-chlorophenyl)methyl}-1H-imidazol-5-yl]-2-(3,4-methylenedioxyphenyl)methyl-2-propenoic acid.

19. A pharmaceutical composition of claim 14 in which the compound is:

(E)-3-[2-n-butyl-1-{(2-chlorophenyl)methyl}-1H-imidazol-5-yl]-2-(4-methoxyphenyl)methyl-2-propenoic acid;

(E)-3-[2-n-butyl-1-{(2-chlorophenyl)methyl}-1H-imidazol-5-yl]-2-benzyl-2-propenoic acid;

(E)-3-[2-n-butyl-1-{(2-chloro-6-fluorophenyl)methyl}-1H-imidazol-5-yl-2-benzyl-2-propenoic acid;

(E)-3-[2-n-butyl-1-{(2-chlorophenyl)methyl}-4-chloro-1H-imidazol-5-yl]-2-benzyl-2-propenoic acid;

(E)-3-[2-n-butyl-1-{(2-chlorophenyl)methyl}-1H-imidazol-5-yl]-2-(3,4-dihydroxyphenyl)methyl-2-propenoic acid;

(E)-3-[2-n-butyl-1-{(2-chlorophenyl)methyl}-1H-imidazol-5-yl]-2-(2-nitrophenyl)methyl-2-propenoic acid;

(E)-3-[2-n-butyl-1-{(2-chlorophenyl)methyl}-1H-imidazol-5-yl]-2-(4-N,N-dimethylaminophenyl)-methyl-2-propenoic acid; or (E)-3-[2-n-butyl-1-{(2-chlorophenyl)methyl}-1H-imidazol-5-yl]-2-(4-aminophenyl)methyl-2-propenoic acid.

20. A method of antagonizing angiotensin II which comprises administering to a subject in need thereof an effective amount of a compound of claim 1.

21. A method of treating hypertension which comprises administering to a subject in need thereof an effective amount of a compound of claim 1.

22. A method of treating congestive heart failure by administering to a subject in need thereof an effective amount of a compound of claim 1.

23. A method of treating renal failure by administering to a subject in need thereof an effective amount of a compound of claim 1.

24. A method of treating glaucoma by administering to a subject in need thereof an effective amount of a compound of claim 1.

* * * * *